United States Patent
Konstantopoulos et al.

(10) Patent No.: US 11,747,338 B2
(45) Date of Patent: *Sep. 5, 2023

(54) USE OF AN INTEGRATED MICROFLUIDIC CHIP FOR ANALYSIS OF CELL MOTILITY AND PREDICTION AND PROGNOSIS OF PATIENT SURVIVAL

(71) Applicant: THE JOHNS HOPKINS UNIVERSITY, Baltimore, MD (US)

(72) Inventors: Konstantinos Konstantopoulos, Ellicott City, MD (US); Colin Paul, Catonsville, MD (US); Alfredo Quinones-Hinojosa, Ponte Vedra Beach, FL (US); Sagar Ramesh Shah, Clemson, SC (US); Alejandro Ruiz-Valls, Baltimore, MD (US); Christopher Yankaskas, Baltimore, MD (US); Juan Carlos Martinez-Gutierrez, Baltimore, MD (US); Bin Sheng Wong, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 951 days.

This patent is subject to a terminal disclaimer.

(21) Appl. No.: 15/780,768

(22) PCT Filed: Dec. 2, 2016

(86) PCT No.: PCT/US2016/064725
§ 371 (c)(1),
(2) Date: Jun. 1, 2018

(87) PCT Pub. No.: WO2017/096232
PCT Pub. Date: Jun. 8, 2017

(65) Prior Publication Data
US 2020/0249232 A1    Aug. 6, 2020

Related U.S. Application Data

(60) Provisional application No. 62/262,158, filed on Dec. 2, 2015.

(51) Int. Cl.
*G01N 33/574* (2006.01)
*B01L 3/00* (2006.01)
*G01N 33/50* (2006.01)

(52) U.S. Cl.
CPC ...... *G01N 33/574* (2013.01); *B01L 3/502761* (2013.01); *G01N 33/5011* (2013.01);
(Continued)

(58) Field of Classification Search
CPC ....... G01N 33/5091; G01N 2800/7028; G01N 33/574; G01N 33/5029; B01L 3/502761;
(Continued)

(56) References Cited

U.S. PATENT DOCUMENTS

2019/0001331 A1* 1/2019 Konstantopoulos .................. G01N 33/5091

FOREIGN PATENT DOCUMENTS

WO    2011158243 A2    12/2011
WO    2015009688 A1    1/2015

OTHER PUBLICATIONS

Huang et al. Evaluation of Cancer Stem Cell Migration Using Compartmentalizing Microfluidic Devices and Live Cell Imaging. Journal of Visualized Experiments. 58: (e3297): Dec. 1-6, 2011.*
(Continued)

*Primary Examiner* — Gailene Gabel
(74) *Attorney, Agent, or Firm* — BALLARD SPAHR LLP

(57) ABSTRACT

The present invention describes an integrated apparatus that enables identification of invasive tumor cells directly from a specimen. The methods using the apparatus can be used to prognose or predict the survivability of the cancer in a
(Continued)

subject and the risk of recurrence of the cancer in the subject after treatment. The methods disclosed herein can be used to determine which chemotherapeutic or other therapies most strongly inhibit the tumor cells invasiveness as a form of personalized therapy.

9 Claims, 17 Drawing Sheets

(52) U.S. Cl.
CPC ..... *G01N 33/5029* (2013.01); *G01N 33/5091* (2013.01); *B01L 2200/0652* (2013.01); *B01L 2300/0816* (2013.01); *B01L 2300/0867* (2013.01); *G01N 2800/7028* (2013.01)

(58) Field of Classification Search
CPC ..... B01L 2200/0652; B01L 2300/0816; B01L 2300/0867
See application file for complete search history.

(56) References Cited

OTHER PUBLICATIONS

Rolli et al. Impact of Tumor Cell Cytoskeleton Organization on Invasiveness and Migration: Microchannel-Based Approach, 5 (1): e872: Jan. 1-8, 2010.*
Boneschansker et al. Microfluidic Platform for the quantitative analysis of leukocyte migration signatures. Nature Communications 5: 4787, pp. 1-12 (Sep. 3, 2014).*
Irimia, D., et al., "Spontaneous migration of cancer cells under conditions of mechanical confinement", Integr. Biol., (2009) vol. 1, pp. 506-512.
Pavesi, A., et al., "Using microfluidics to investigate tumor cell extravasation and T-cell immunotherapies", Eng Med Biol Soc (EMBC) (2015) pp. 1853-1856.
Rolli, C., et al., "Impact of tumor cell cytoskeleton organization on invasiveness and migration: a microchannel-based approach", PLoS ONE (2010) vol. 5, No. 1, e8726.
Zeta Y., et al., "Microfluidic modeling of cancer metastasis" Cells, Forces and the Microenvironment, Chapter Seventeen (2014).
Balzer, et al., c-Src differentially regulates the functions of microtentacles and invadopodia. Oncogene 29, 6402-6408 (2010).
Balzer, et al., Antimitotic chemotherapeutics promote adhesive responses in detached and circulating tumor cells. Breast cancer research and treatment 121, 65-78 (2010).
Balzer, et al., Physical confinement alters tumor cell adhesion and migration phenotypes. Faseb J 26, 4045-4056 (2012).
Barkan, et al., Inhibition of metastatic outgrowth from single dormant tumor cells by targeting the cytoskeleton. Cancer Res 68, 6241-6250 (2008).
Chambers, et al., Dissemination and growth of cancer cells in metastatic sites. Nat Rev Cancer 2, 563-572 (2002).
Charpentier, et al., Curcumin targets breast cancer stem-like cells with microtentacles that persist in mammospheres and promote reattachment. Cancer Res 74, 1250-1260 (2014).
Chen, et al., Mesolethin Binding to CA125/MUC16 Promotes Pancreatic Cancer Cell Motility and Invasion via MMP-7 Activation. Scientific reports 3, 1870 (2013).
Crowder, et al., PIK3CA and PIK3CB inhibition produce synthetic lethality when combined with estrogen deprivation in estrogen receptor-positive breast cancer. Cancer Res 69, 3955-3962 (2009).
Dharmawardhane, et al., Localization of p21-activated kinase 1 (PAK1) to pinocytic vesicles and cortical actin structures in stimulated cells. J Cell Biol 138, 1265-1278 (1997).
Even-Ram, et al., Myosin IIA regulates cell motility and actomyosin-microtubule crosstalk. Nature cell biology 9, 299-309 (2007).
Fraley, et al., A distinctive role for focal adhesion proteins in three-dimensional cell motility. Nature cell biology 12, 598-604 (2010).
Friedl, et al., Cancer Invasion and the Microenvironment: Plasticity and Reciprocity. Cell 147, 992-1009 (2011).
Hekimian, et al., Epithelial cell dissemination and readhesion: analysis of factors contributing to metastasis formation in breast cancer. ISRN oncology 2012, 601810 (2012).
Hung, et al., Distinct signaling mechanisms regulate migration in unconfined versus confined spaces. J Cell Biol 202, 807-824 (2013).
Ibrahim, et al., PI3K inhibition impairs BRCA1/2 expression and sensitizes BRCA-proficient triplenegative breast cancer to PARP inhibition. Cancer discovery 2, 1036-1047 (2012).
Wolf, et al., Collagen-based cell migration models in vitro and in vivo. Seminars in cell & developmental biology 20, 931-941 (2009).
Karabacak, et al., Microfluidic, marker-free isolation of circulating tumor cells from blood samples. Nat Protoc 9, 694-710 (2014).
Kiessling, et al., Analysis of multiple physical parameters for mechanical phenotyping of living cells. Eur Biophys J 42, 383 (2013).
Kim, et al., Focal adhesion size uniquely predicts cell migration. FASEB J 27, 1351-1361 (2013).
Martin, et al., Activated phosphatidylinositol 3-kinase is sufficient to mediate actin rearrangement and GLUT4 translocation in 3T3-L1 adipocytes J Biol Chem 271, 17605-17608 (1996).
Martin, et al., A cytoskeleton-based functional genetic screen identifies Bcl-xL as an enhancer of metastasis, but not primary tumor growth. Oncogene 23, 4641-4645 (2004).
Matrone, et al., Metastatic breast tumors express increased tau, which promotes microtentacle formation and the reattachment of detached breast tumor cells. Oncogene 29, 3217-3227 (2010).
Matrone, et al., Microtentacles tip the balance of cytoskeletal forces in circulating tumor cells. Cancer Res 70, 7737-7741 (2010).
Mendez, et al., Vimentin induces changes in cell shape, motility, and adhesion during the epithelial to mesenchymal transition. FASEB J 24, 1838-1851 (2010).
Pal, et al., Three Dimensional Cultures: A Tool To Study Normal Acinar Architecture vs. Malignant Transformation of Breast Cells. Journal of visualized experiments: JoVE 25, (2014).
Patsialou, et al., Selective gene-expression profiling of migratory tumor cells in vivo predicts clinical outcome in breast cancer patients. Breast cancer research : BCR 14, R139 (2012).
Zhuang, et al., Evidence for microtubule target engagement in tumors of patients receiving ixabepilone. Clinical cancer research : an official journal of the American Association for Cancer Research 13, 7480-7486 (2007).
Raman, et al., Probing cell traction forces in confined microenvironments. Lab Chip 13, 4599-4607 (2013).
Ridley, et al., Cell migration: integrating signals from front to back. Science 302, 1704-1709 (2003).
Yu, Z., et al., "Microfluidic modeling of cancer metastasis", Forces and the Microenvironment, Chapter Seventeen, (2014), pp. 1, 11, 15.
Shen, et al., Ixabepilone, a novel microtubule-targeting agent for breast cancer, is a substrate for P-glycoprotein (P-gp/MDR1/ABCB1) but not breast cancer resistance protein (BCRP/ABCG2). The Journal of pharmacology and experimental therapeutics 337, 423-432 (2011).
Stroka, et al., Water permeation drives tumor cell migration in confined microenvironments. Cell 157, 611-623 (2014).
The Physical Sciences—Oncology Centers Network, A physical sciences network characterization of nontumorigenic and metastatic cells Scientific reports 3, 1449 (2013).
Tong, et al., Chemotaxis of cell populations through confined spaces at single-cell resolution. PLoS One 7, e29211 (2012).
Tong, et al., Selectin-mediated adhesion in shear flow using micropatterned substrates: multiple-bond interactions govern the critical length for cell binding. Integrative biology : quantitative biosciences from nano to macro 4, 847-856 (2012).
Vidi, et al., Three-dimensional culture of human breast epithelial cells: the how and the why. Methods in molecular biology 945, 193-219 (2013).

(56) References Cited

OTHER PUBLICATIONS

Vitolo, et al., Loss of PTEN induces microtentacles through PI3K-independent activation of cofilin. Oncogene 32, 2200-2210 (2013).

Weigelin, et al., Intravital third harmonic generation microscopy of collective melanoma cell invasion: Principles of Interface guidance and microvesicle dynamics. IntraVital 1, 32-43 (2012).

Whipple, et al., Vimentin filaments support extension of tubulin-based microtentacles in detached breast tumor cells. Cancer Res 68, 5678-5688 (2008).

Whipple, et al., Epithelial-to-mesenchymal transition promotes tubulin detyrosination and microtentacles that enhance endothelial engagement. Cancer Res 70, 8127-8137 (2010).

Wildt, et al., Programmed subcellular release for studying the dynamics of cell detachment. Nat Methods 6, 211-213 (2009).

Wirtz, et al., Particle-tracking microrheology of living cells: principles and applications. Annual review of biophysics 38, 301-326 (2009).

Wirtz, et al., The physics of cancer: the role of physical interactions and mechanical forces in metastasis. Nat Rev Cancer 11, 512-522 (2011).

* cited by examiner

F-actin  Rac1  Cdc42
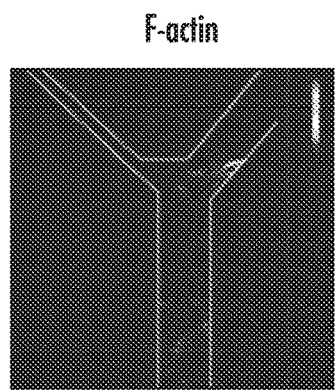 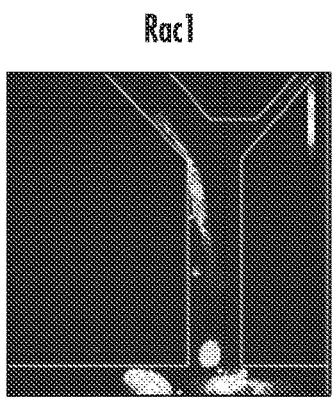 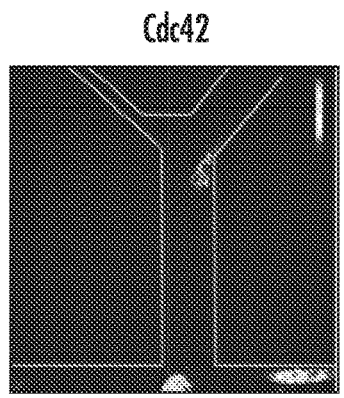
FIG. 3A  FIG. 3B  FIG. 3C
TO 20 μm BRANCH
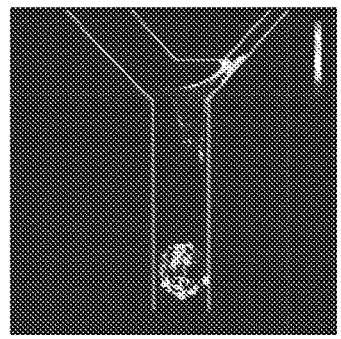 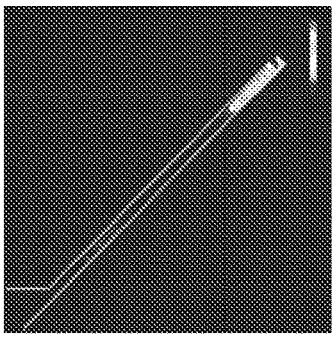 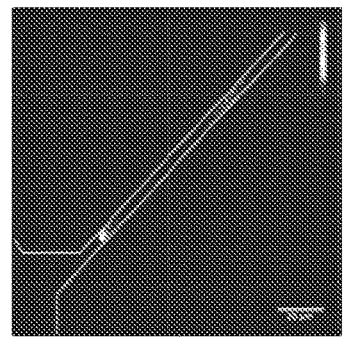
FIG. 3D  FIG. 3E  FIG. 3F
TO 3 μm BRANCH

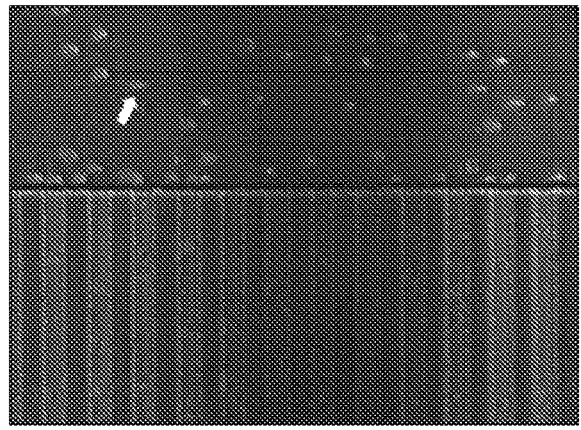
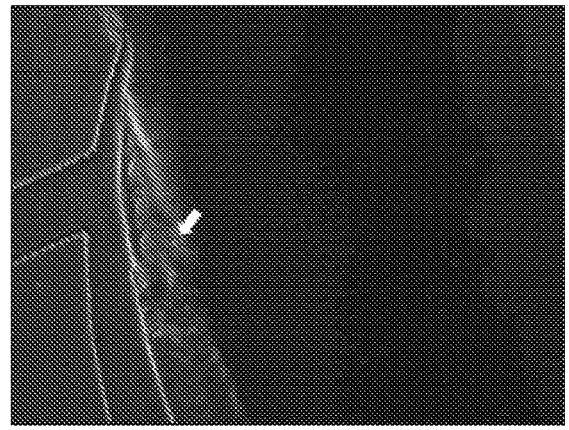
FIG. 6A  FIG. 6B
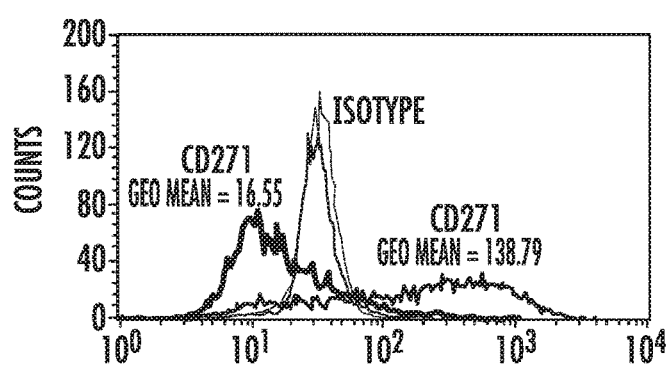
BULK CELLS (FROM CULTURE) - GREEN;
ISOLTED CELLS - BLUE
FIG. 6C

MIGRATORY CELLS     CONTROL CELLS

| CELL LINE | METASTATIC | TUMOR-INITIATING CELLS | % MIGRATORY CELLS |
|---|---|---|---|
| HMLE Luc 26 | NO (NORMAL) | - | 0.5±0.8 |
| HMLE Luc 8 | NO (NORMAL) | - | 1.6±1.6 |
| 184B5 | NO (NORMAL) | - | 1.5±2.0 |
| 184A1 | NO (NORMAL) | - | 5.7±8.0 |
| MCF-10A | NO (NORMAL) | - | 3.0±2.9 |
| MCF-12F | NO (NORMAL) | - | 3.3±4.7 |
| HCC1428 | NO | + | 0±0 |
| ZR75-1 | NO | + | 0±0 |
| MDA-MB-468 | NO | + | 0±0 |
| SkBr3 | NO | + | 0±0 |
| BT-20 | NO | + | 0±0 |
| MCF7 TARGETED WT | NO | + | 1.2±1.0 |
| MCF-7 | NO | + | 2.9±3.7 |
| MCF7 Her2 | NO | + | 5.4±8.9 |
| MCF7-Luciferase | NO | + | 6.5±5.8 |
| T47D | NO | + | 4.2±4.6 |
| SUM149 | YES | ++ | 1.2±1.0 |
| MDA-MB-436 | YES | +++ | 8.7±0.5 |
| Hs578t | YES | +++ | 16±2.0 |
| BT-549 | YES | +++ | 18±3.5 |
| K-Ras/OBSCN-KD MCF10A | YES | +++ | 20 |
| MDA-MB-231 TUMOR | YES | +++ | 15±4.5 |
| MDA-MB-231 | YES | +++ | 17±5.0 |
| MDA-MB-231 LungMet | YES | +++ | 25±6.8 |
| MDA-MB-231 CTC | YES | +++ | 46±1.8 |
| SUM159 | YES | +++ | 30±1.4 |
| A375 | YES | +++ | 38±7 |

FIG. 8

| CELL LINE | METASTATIC | TUMOR-INITIATING CELLS | CONTROL % MIGRATORY CELLS | PI3K INHIBITION % MIGRATORY CELLS |
|---|---|---|---|---|
| MDA-MB-436 | YES | +++ | 13 ±7% | 18 ±7% |
| MDA-MB-231 | YES | +++ | 22 ±3% | 34 ±8% |
| Bt-549 | YES | +++ | 32 ±8% | 19 ±1% |
| Hs578t | YES | +++ | 20 ±7% | 15 ±2% |

(TNBC)

*FIG. 9*

LENS-FREE HOLOGRAPHY

PHASE CONTRAST MICROSCOPY

PHASE + FLUORESCENCE MICROSCOPY

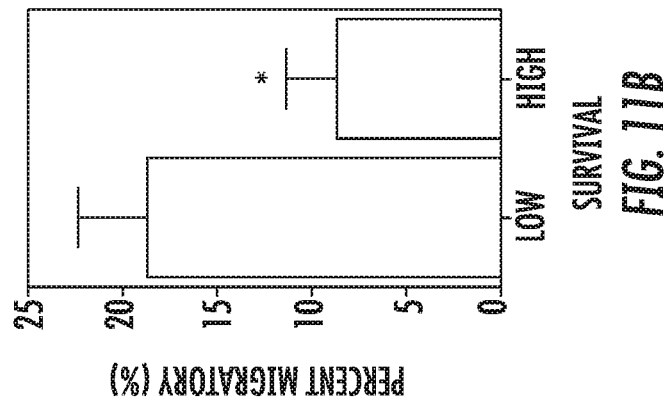
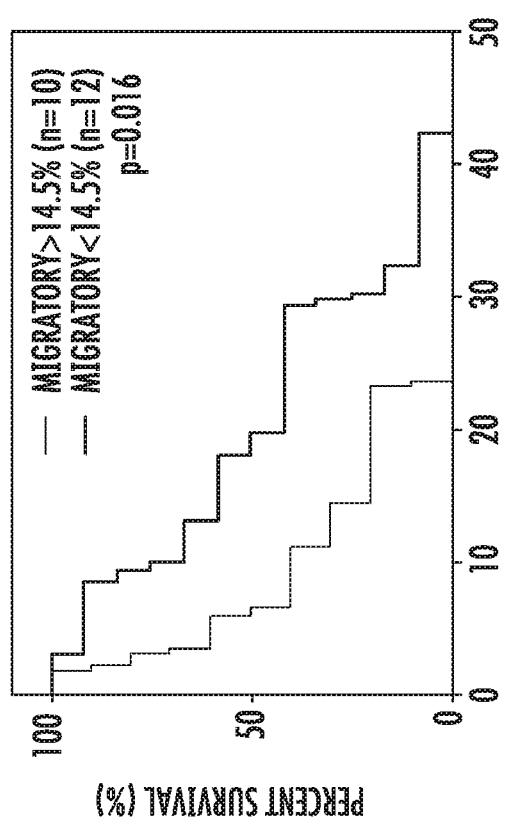

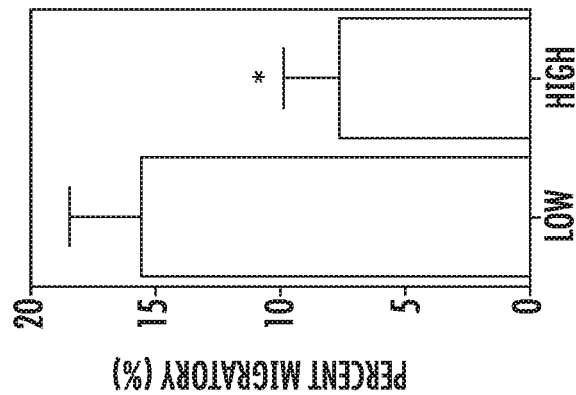
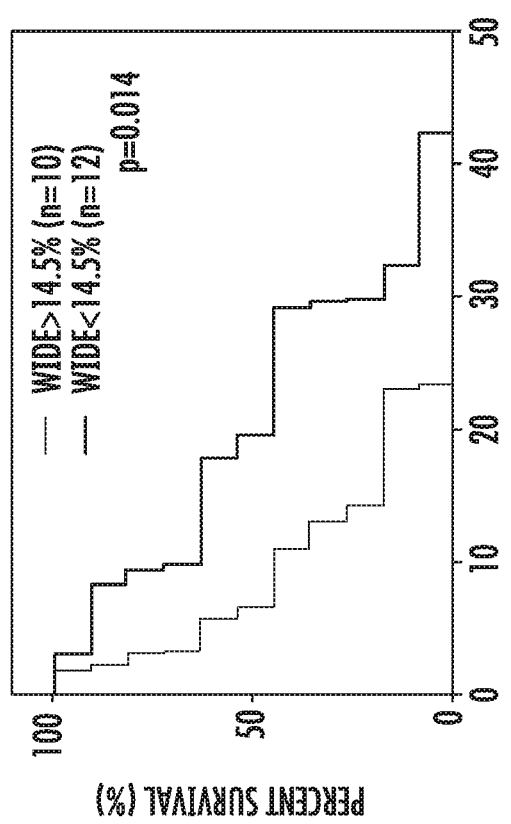
FIG. 12B
FIG. 12A
| % MIGRATORY | NUMBER | MEDIAN SURVIVAL (MONTHS) |
|---|---|---|
| <11.4% | 11 | 19.7 |
| >11.4% | 11 | 6.5 |
FIG. 12C

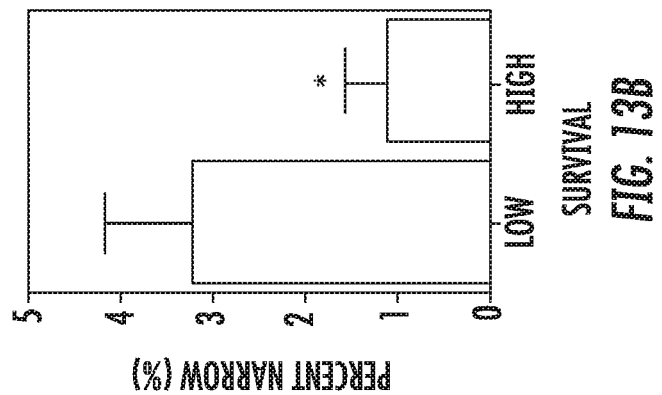
FIG. 13B
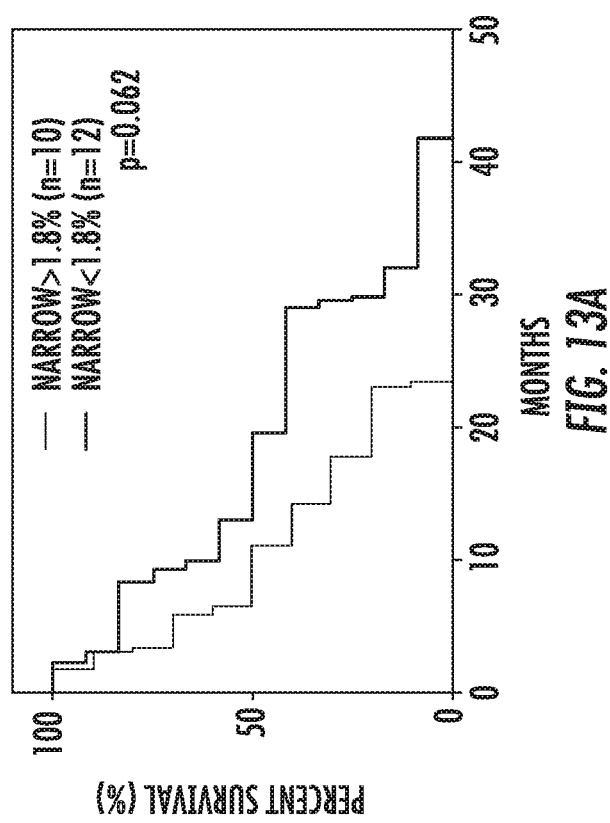
FIG. 13A
| % MIGRATORY | NUMBER | MEDIAN SURVIVAL (MONTHS) |
|---|---|---|
| <1.8% | 12 | 16.5 |
| >1.8% | 10 | 8.9 |
FIG. 13C

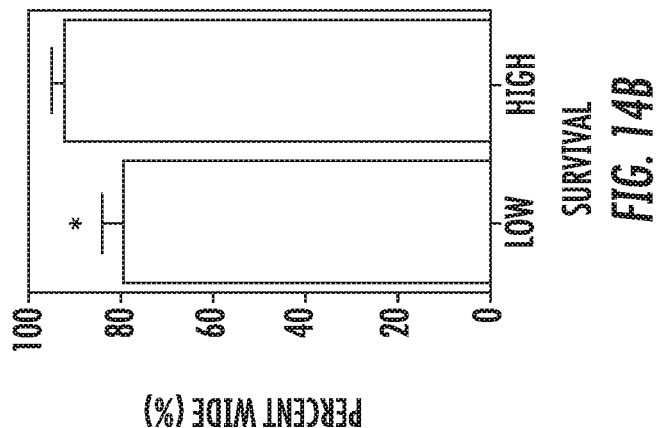
FIG. 14B
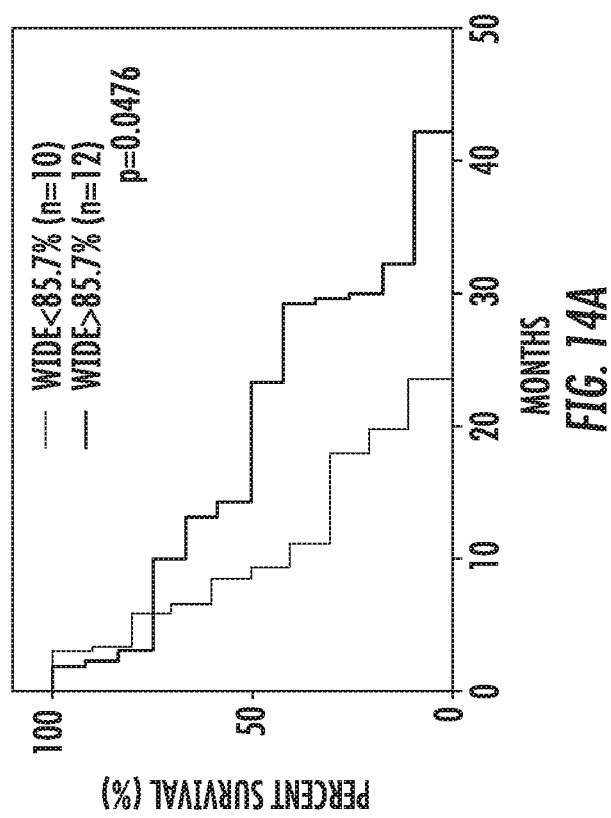
FIG. 14A
| % MIGRATORY | NUMBER | MEDIAN SURVIVAL (MONTHS) |
|---|---|---|
| <85.7% | 10 | 8.9 |
| >85.7% | 12 | 18.8 |
FIG. 14C

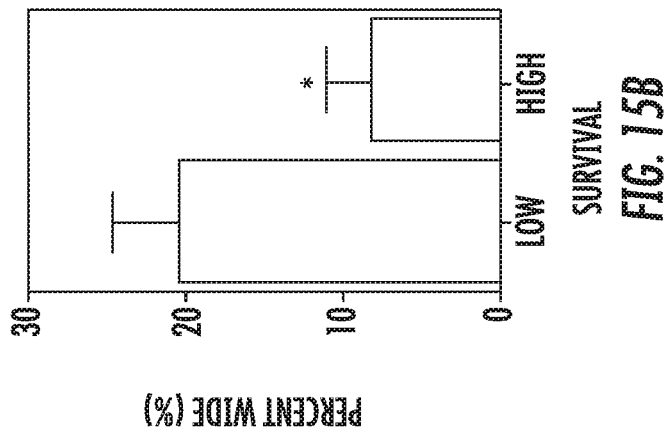
FIG. 15B
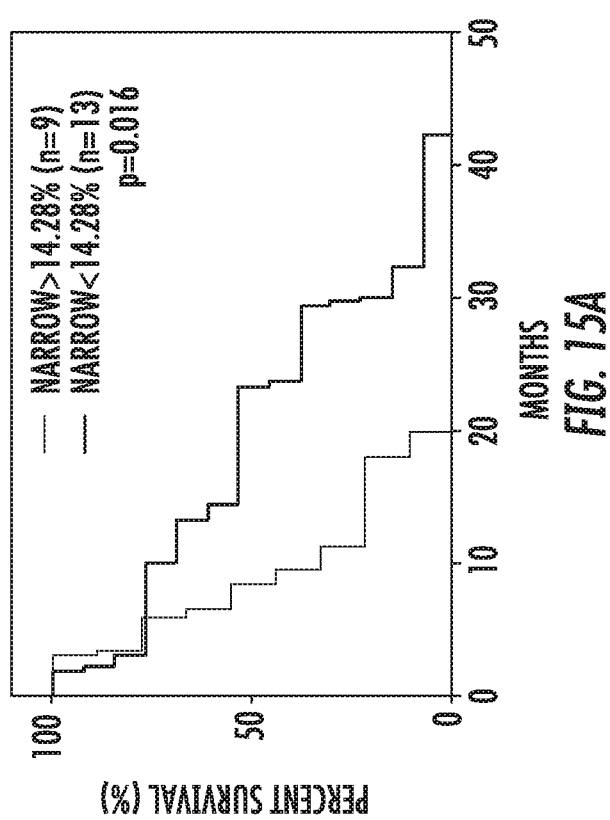
FIG. 15A
FIG. 15C

USE OF AN INTEGRATED MICROFLUIDIC CHIP FOR ANALYSIS OF CELL MOTILITY AND PREDICTION AND PROGNOSIS OF PATIENT SURVIVAL

CROSS-REFERENCE TO RELATED APPLICATIONS

This application is a 35 U.S.C. § 371 U.S. national entry of International Application PCT/US2016/064725, having an international filing date of Dec. 2, 2016, which claims the benefit of U.S. Provisional Application No. 62/262,158, filed Dec. 2, 2015, the content of each of the aforementioned applications is herein incorporated by reference in their entirety.

STATEMENT OF GOVERNMENTAL INTEREST

This invention was made with government support under grant no. CA183804 awarded by the National Institutes of Health. The government has certain rights in the invention.

BACKGROUND OF THE INVENTION

Personalized medical plans aiming to limit metastasis are difficult to develop. The current state of the art requires the expansion of human cancers in immunodeficient mice before the cancers can be subjected to drug screenings. It is known that metastatic subpopulations of cancer cells have heightened motility which is linked to aggressiveness and invasiveness of the cancer. The ability to identify such a subpopulation of cells in a tumor of a patient would be useful in classifying the aggressiveness or metastatic potential of the cancer in the subject, and would also be useful in identifying optimal courses of treatment and determining whether the treatment was effective.

Until recently, there currently existed no means for determining the motility of a cell or subpopulation of cells in a sample, using assays which are low cost, high throughput, and easy to operate. The present inventors previously created a microfluidic apparatus which is capable of identifying a cell and/or subpopulation of cells that have a significantly increased motility compared to the cell population as a whole, and which the inventors have shown to be correlated with metastatic potential in a number of solid tumor types. However, there still is an unmet need in the ability of clinicians and investigators to identify patients with brain cancer that is highly invasive and which correlates with lower survival times and high risk of recurrence.

SUMMARY OF THE INVENTION

In accordance with an embodiment, the present invention provides a method for identifying the invasiveness of a brain cancer cell or population of cells in a sample comprising: a) obtaining a cell or population of cancer cells derived from the sample of a tumor; b) incubating the cells for a period time in a integrative microfluidic apparatus; c) imaging the cells in the apparatus for a period of time; and d) determining whether a cell or subpopulation of cells in the sample are invasive.

In accordance with an embodiment, the present invention provides a method for predicting and/or prognosing a brain tumor patient survival and/or recurrence comprising: a) obtaining a cell or population of cells from the tumor of a patient; b) adding a sufficient sample of the cells from the tumor to an integrated microfluidic apparatus; c) incubating the cells for a period time in a integrative microfluidic apparatus; d) imaging the cells in the integrated microfluidic apparatus for a period of time; e) determining whether a cell or subpopulation of cells in the sample are invasive; and; f) identifying the tumor of the subject as having low survivability or a high risk of recurrence when the proportion of invasive cells is greater than about 5% to about 50% of the all cells.

In accordance with a further embodiment the present invention provides a method for identifying an effective chemotherapeutic treatment regimen in a subject having a tumor.

An effective chemotherapeutic treatment regimen is treating a subject with one or more chemotherapeutic agents that will significantly decrease the proportion of migratory cells from the subject, as determined using the apparatus and methods described herein, and therefor inhibit invasiveness of the tumor cells in the subject. Multiple devices can be operated in parallel to screen a number of therapeutic agents.

In accordance with an embodiment, the present invention provides a method for identifying an agent which inhibits the invasiveness of a cell or population of tumor cells in a sample comprising: a) adding to the integrated microfluidic apparatus an a cell or population of cells from the sample and the test agent; b) incubating the cells for a period time; c) imaging the cells in the apparatus for a period of time; d) comparing the images of the cells in the integrated microfluidic apparatus over time; e) identifying a cell or subpopulation of cells in the sample as invasive when the cell or subpopulation of cells migrates past the bifurcation of any of the migratory channels of the apparatus into either of the one or more outlet ends of the migration channels of the integrated microfluidic apparatus and/or exits out of the migration channels; f) comparing the number and/or extent of invasiveness of the cell or subpopulation of cells to the number and/or extent of migration of the cell or subpopulation of cells of e) to the number and/or extent of migration of a control cell or subpopulation of cells migrating in the absence of the agent.

BRIEF DESCRIPTION OF THE DRAWINGS

FIG. 3 shows fluorescent on-chip imaging of F-actin and Rho GTPases. MDA-MB-231 cells within the microchannels were fixed and stained for (3 A,D) F-actin, (3 B,E) Rac1, or (3 C,F) Cdc42. Panels 3A-C show cells entering the 20 μm-wide branch channel. Panels 3D-F show cells entering or migrating within the 3 μm-wide branch channel. Non-migratory cells are shown at the 20 μm-wide channel bases in panels B and D (arrows).

FIG. 6 depicts the extraction of migratory A375 cells from a microchannel cell migration device of the present invention. (6A) Trypsinized cells flowed in the upper medium line without entering the microchannels. Arrow indicates cell that has been completely detached from the device. (6B) Detached cells flowed to the upper medium outlet well. Arrow indicates cell entering the well. (C) Extracted A375 cells were expanded using standard cell culture techniques for 20 days and assayed for surface protein expression levels of the cancer stem cell marker CD271 using flow cytometry. A375 cells that had migrated through the device and been expanded (blue) exhibited higher surface protein expression levels of CD271 than the bulk A375 cell population (green).

FIG. 8 enumerates the percentage of migratory cells as determined using the present invention for a panel of breast epithelial or cancer cell lines. Nonmetastatic cell lines displayed low levels of migration in the device (less than or equal to 6.8% of cells entering the migration channels reached the branch channels following the bifurcation). In contrast, metastatic cell lines contained a migratory subpopulation (from about 8.2 to about 46% of the cells from each cell line scored as migratory in the present invention).

FIG. 9 demonstrates the differential response of triple-negative breast cancer (TNBC) cell lines to an example pharmacological agent. MDA-MB-436, MDA-MB-231, Bt549, and Hs578t cells were treated with 10 μM LY294002, an inhibitor of PI3K, or the appropriate control. Migration of MDA-MB-231 cells in the invention increased, while migration of Bt549 cells decreased. A similar percentage of MDA-MB-436 and Hs578t cells were migratory in the presence or absence of the inhibitor.

FIG. 11: Overall Survival—% Migratory: (FIG. 11a) Kaplan-Meier survival of patients with >14.28% vs <14.28% migratory cells. This cutoff was established by computing the mean % migratory value and separating the patients above or below this mean value. Log-Rank (Mantel Cox) test showed significant difference between the curves although. Table (FIG. 11c) lists median survival in months for each of the above-mentioned groups (FIG. 11b). Separating patients as lower than expected survival of 14.6 months (this is taken from the classic StuppR. NEJM paper establishing the current standard of care) and higher than expected. Average percent migratory cells with SEM is represented. T-test demonstrates significant different between the two groups.

FIG. 12: Overall Survival—% Wide Entry of All Cells: (FIG. 12a) Kaplan-Meier survival of patients with >11.4% vs <11.4% migratory cells which migrated into the wide outlet channel. This cutoff was established by computing the mean % Wide entry of all cells value and separating the patients above or below this mean value. Log-Rank (Mantel Cox) test showed significant difference between the curves although. Table (FIG. 12c) lists median survival in months for each of the above-mentioned groups. (FIG. 12b) Separating patients as lower than expected survival of 14.6 months (using the StuppR. NEJM paper methodology) and higher than expected. Average percent wide entry of all cells with SEM is represented. T-test demonstrates significant different between the two groups.

FIG. 13: Overall Survival—% Narrow Entry of All Cells: (FIG. 13a) Kaplan-Meier survival of patients with >1.8% vs <1.8% migratory cells which migrated into the narrow outlet channel. This cutoff was established by computing the mean % narrow entry of ALL cells value and separating the patients above or below this mean value. Log-Rank (Mantel Cox) test showed significant difference between the curves although. Table (FIG. 13c) lists median survival in months for each of the above-mentioned groups. (FIG. 13b) Separating patients as lower than expected survival of 14.6 months (using the StuppR. NEJM paper) and higher than expected. Average percent narrow entry of all cells with SEM is represented. T-test demonstrates significant different between the two groups.

FIG. 14: Overall survival—% Wide entry of Migratory cells: (FIG. 14a) Kaplan-Meier survival of patients with >85.7% vs <85.7% Wide channel entry of migratory cells. This cutoff was established by computing the mean % Wide entry of migratory cells value and separating the patients above or below this mean value. Log-Rank (Mantel Cox) test showed significant difference between the curves although. Table (FIG. 14c) lists median survival in months for each of the above-mentioned groups (FIG. 14b) Separating patients as lower than expected survival of 14.6 months (using the StuppR. NEJM paper methodology) and higher than expected. Average percent wide entry of migratory cells with SEM is represented. T-test demonstrates significant different between the two groups.

FIG. 15: Overall survival—% Narrow entry of Migratory cells: (FIG. 15a) Kaplan-Meier survival of patients with >14.28% vs <14.28% narrow channel entry of migratory cells. This cutoff was established by computing the mean % narrow entry of migratory cells value and separating the patients above or below this mean value. Log-Rank (Mantel Cox) test showed significant difference between the curves although. Table (FIG. 15c) lists median survival in months for each of the abovementioned groups. (FIG. 15b) Separating patients as lower than expected survival of 14.6 months (using the StuppR. NEJM paper methodology) and higher than expected. Average percent narrow entry of migratory cells with SEM is represented. T-test demonstrates significant different between the two groups.

FIG. 17 depicts the effects that the cutoff (%) and the duration of time that cell migration is observed for on the ability of the invention to predict whether a cell line is metastatic or nonmetastatic. Data is shown for the cell lines described in FIG. 8.

DETAILED DESCRIPTION OF THE INVENTION

Figure 1A:
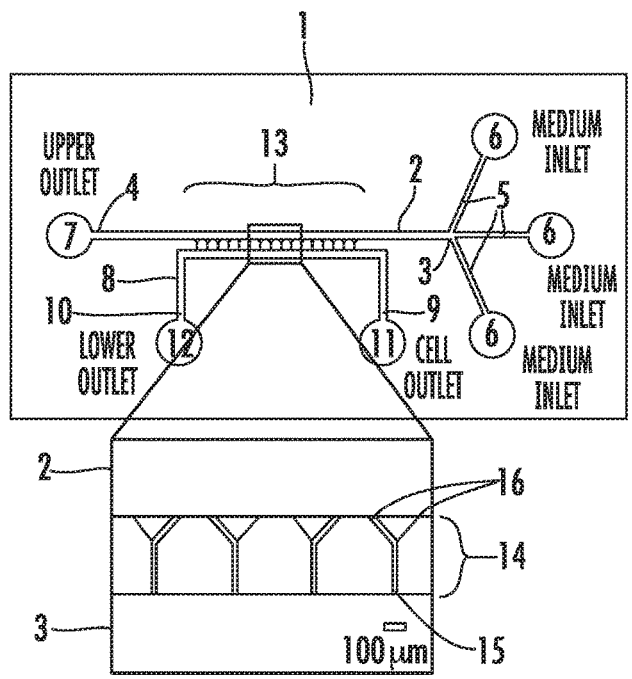
FIG. 1 illustrates an embodiment of the apparatus used in the methods of the present invention. (1A) A schematic of device, showing overall design of an embodiment used in the methods disclosed herein. Inset shows details of Y-shaped microchannels. (1B) Schematic of completed PDMS device bonded to glass coverslip. (1C) Schematic of cells seeded at channel bases. (1D) Phase contrast image of MDA-MB-231 cells migrating in 200 µm-long Y-shaped microchannels.

The present invention describes methods for identifying a cell or population of cells from a tumor of a subject that are invasive compared to the population of tumor cells as a whole, using an integrated microfluidic apparatus that enables identification of these migratory cells directly from a specimen. These methods and apparatus were first described in International Patent Publication No. WO 2015/009688, filed Jul. 15, 2014, and incorporated by reference herein as if set forth in its entirety.

The integrated microfluidic apparatus only requires a small number of cells to perform an assay. The apparatus used in the methods of the present invention includes novel topographic features which can reliably differentiate between migratory and non-migratory cell populations in a sample. Furthermore, in some embodiments, both the spontaneous and chemotactic migration of cancer cells may be measured to distinguish between subpopulations within a tumor sample. The migratory cells identified using the apparatus and methods of the present invention may be separated and further analyzed to distinguish factors promoting metastasis within the population. Cells in the apparatus can be treated with chemotherapeutic or other agents to determine drug strategies to most strongly inhibit migration. The use of optically transparent materials in some embodiments allows a wide range of imaging techniques to be used for in situ imaging of migratory and non-migratory cells in the apparatus. The apparatus and methods of the present invention are useful for predicting the invasive propensity of brain tumor cells, predicting survival times and/or risk of recurrence of tumors post-operatively for patients and selecting optimal drugs for personalized therapies.

In an embodiment, the integrated microfluidic apparatus comprises a substrate in the form of a chip having a plurality of layers. In one embodiment, the chip comprises a fluid layer and a coverslip layer, which are bonded together at final assembly of the apparatus. The fluid layer is composed of a plurality of channels having at least one or more inlets and outlets.

In an embodiment, the fluid layer of the integrated microfluidic apparatus of the present invention comprises at least two channels, each having at least one or more inlets which communicate with a reservoir, and each channel also having at least one or more outlets which communicate with a reservoir. The channels can have any dimension within the limits of the depth of the substrate. In some embodiments, the channels can have dimensions of about 3 μm to about 15 μm in height, about 3 μm to about 50 μm in width, and about 100 μm to about 400 μm in length. There can be any number of channels limited only by the dimensions of the chip used. In some embodiments, the chip can comprise greater than 200 channels.

Within the fluid layer of the substrate, in some embodiments, there are at least two channels, a first channel, also termed "a medium channel" which can be filled with any type of biological media or solvent. There is also at least a second channel, also termed "a cell channel" which can be filled with any type of biological media or solvent that contains a sample of cells to be assayed. In an embodiment, the first and second channels are disposed in proximity to each other and are parallel into at least a portion of the two channels in the fluid layer of the substrate. The first and second channels have at least one inlet portion which can be the same or have a smaller dimension than the main portion of the first and second channel. Each inlet portion is connected to the inlet end of the first and second channel and communicates with the channels. Each inlet portion is also in communication with a reservoir wherein media or fluid can be introduced into the inlet of the channel.

The first and second channels have at least one outlet portion which is the same dimension as the main portion of the first and second channel. Each outlet portion is connected to the outlet end of the first and second channel and communicates with the channels. Each outlet portion is also in communication with a reservoir wherein media or fluid can be directed to or removed from the channel.

In one or more embodiments, a novel aspect of the integrated microfluidic apparatus of the present invention is located in the migratory channel portion of the apparatus. In an embodiment, the migratory channel portion is an area where the first channel and second channel are in proximity to each other and are connected by a plurality of migratory channels having at least one inlet and at least one or more outlets. The migratory channels, in some embodiments, are bifurcated at a point distal from the inlet portion of the migratory channel. In some embodiments, the bifurcation results in two outlet ends of the migratory channel which communicate with the media channel. These channels are significantly reduced in size, for example, by approximately by a factor of 10, so as to allow one cell body at a time to enter the migratory channel from the cell channel. For example, in an embodiment, the main portion of the first and second channels has a width of about 400 µm and a height of about 50 µm, whereas the migratory channels have an inlet portion which communicates with the second channel and has a width of about 20 µm and a height of about 10 µm. In some embodiments, the migratory channels can have dimensions of width of about 3 µm to about 50 µm, and a height of about 3 µm to about 15 µm. The one or more outlet portions of the migratory channels can have the same or different widths than the inlet portion of the migratory channel. The bifurcation angle of the migratory channels is about 30° to 70° from the horizontal, which is defined as the long axis of the first and second channels. It is in these migratory channels that the cells in the sample are assayed for their ability to transverse the migratory channels and their speed, physical and biochemical characteristics can be measured.

Referring now to FIG. 1A which depicts an embodiment of the integrated microfluidic apparatus used in the methods of the present invention, the fluid layer of the substrate is shown generally as (1) and is composed of a polydimethylsiloxane (PDMS) chip molded from a negative replica on a silicon wafer on which photolithography has been used to create a plurality of channels. A first channel (2), which has an inlet portion (3) and an outlet portion (4). The inlet portion is in communication with three inlets (5), termed "medium inlets" which are channels in the substrate that communicate between the inlet portion (3) and an inlet reservoir (6). The outlet portion (4) is in communication with an outlet reservoir (7), termed "upper outlet." On the fluid layer is also disposed a second channel (8), termed "cell channel" which has an inlet portion (9) and an outlet portion (10). The inlet portion (9) of the second channel is in communication with an inlet reservoir (11), termed "cell inlet." The outlet portion (10) of the second channel is in communication with an outlet reservoir (12), termed "lower outlet." In some embodiments, the inlet and outlet reservoirs are punched into the substrate of the coverslip layer having a circular shape and a diameter of about 6 mm, although that is only limited by the size of the volume required and the space available on the substrate.

On the fluid layer there is a migratory channel portion (13) which is a region between the first channel (2) and second channel (3) that has a plurality of migratory channels (14) which communicate with the first and second channels. As seen on the exploded inset in FIG. 1A, the migratory channels (14) have an inlet end (15) which communicates with the second channel (3), and two or more outlet ends (16), which are in communication with the first channel (2). The two or more outlet ends (16) are the result of a bifurcation (17) of the migratory channel and a point distal from the inlet end (15) of the migratory channel. In an embodiment, there are about 16 migratory channels (14) which connect the first (2) and second (3) channels in the migratory channel portion (13) of the fluid layer.

In an alternative embodiment, there are about 240 migratory channels (14) which connect the first (2) and second (3) channels in the migratory channel portion (13) of the fluid layer.

In some embodiments, the first and second channels are between about 10 mm to about 50 mm in length, and have a height/depth of between about 30 µm to about 100 µm, and a width of about 100 µm to about 400 µm. In some embodiments, the inlets for the first and second channels have a length of between 2 mm to about 10 mm, a height/depth of between about 30 µm to about 100 µm, and a width of about 50 µm to about 400 µm. In some embodiments, the migratory channels have a length of between about 200 to 400 µm, a height/depth of between about 3 µm to about 15 µm, and a width between about 3 µm to about 50 µm.

Figure 1B:
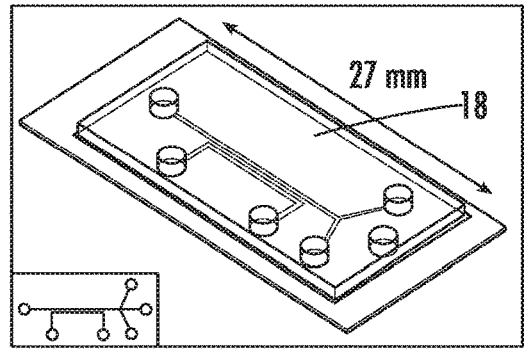

As seen in FIG. 1B, the apparatus has a coverslip layer (18) which in whole, or in part, is made of an optically transparent substrate. Any optically substrate which is compatible with the fluid layer substrate can be used. In an embodiment, the coverslip layer is formed of glass. It will be understood by those of ordinary skill that the portion of the coverslip layer that is optically transparent will allow visualization and imaging of the cells in the apparatus in real time. The coverslip is bonded using a variety of known means. In an embodiment, the coverslip is bonded to the fluid layer via plasma treatment of about 18 W for a sufficient time, for example, about 2 minutes.

Before use, the fluid layer channels are all treated with a solution of collagen, for example, a solution of about 20 µg/ml collagen, such as rat tail collagen type I, for about an hour at 37° C., and then the channels are washed with PBS or similar buffer. In some embodiments, other extracellular proteins, such as laminin, fibronectin, VCAM-1, hyaluronic acid, or gelatin, are used instead of collagen.

The apparatus can be used for a variety of assays to detect and quantify the micromechanical, morphological, and molecular signatures of migratory and non-migratory cells in the device.

Generally, operation of the apparatus comprises a first wash of the first channel and media inlet reservoirs (6) with a medium free buffer such as DPBS. This is followed by seeding of cells of interest from a sample. Cells of interest are seeded or introduced into the cell inlet reservoir (11) of the second channel. In some embodiments, the cells are trypsinized and suspended in serum free medium at a concentration of about $1 \times 10^5$ to about $5 \times 10^6$ cells/ml. In an embodiment, the cells are suspended at a concentration of about $2 \times 10^6$ cells/ml. About a 50 µl aliquot of the cell suspension is introduced into the cell inlet reservoir (11), and the cells are incubated a 37° C. for a time sufficient to allow the cells to seed at the base of the migratory channels (14), for example, about 2 to about 30 minutes, preferably between about 5 to about 10 minutes. In an embodiment, about 10 µl to 50 µl of a suitable biological medium or buffer are introduced to the lowermost medium inlet reservoir (6) to prevent convective flow of cells through the migratory channels (14). Any remaining cells in the cell inlet reservoir (11) are then removed. Cell seeding is followed by introduction of a suitable biological medium or buffer into the media channel of the apparatus via the medium inlet reservoirs (6) and the flow is in the direction of the upper outlet (FIG. 1A). A suitable biological medium or buffer is also introduced into the cell inlet reservoir (11) of the second channel. The apparatus can be manipulated to either induce a chemoattractant gradient across the migratory channels, or not to have any chemoattractant gradient. When inducing a gradient, biological medium or buffer containing the chemoattractant is introduced into the uppermost medium inlet reservoir (6), with biological medium or buffer without the chemoattractant introduced into the remaining medium inlet reservoirs (6), and into the cell inlet reservoir (11) of the second channel. This creates a chemoattractant gradient across the migratory channels (14). If no gradient is desired, the medium inlet reservoirs (6) and cell inlet reservoir (11) are filled with the same biological medium or buffer. In some embodiments, other biologically active compounds or molecules can be added to the cell suspension when the cells are introduced into the apparatus, or after the cells have been seeded, to perform a variety of experiments.

It will be understood by those of skill in the art that the methods of operation described herein are only exemplary. These methods can be altered to suit the experimental conditions as needed, and the steps can be manipulated or changed accordingly.

In exemplary operation, the integrated microfluidic apparatus is placed in a temperature and $CO_2$ controlled incubator, imaging chamber or stage type device, to which is mounted an imaging system. In some embodiments, the migrating cells are imaged at 10× magnification using a phase contrast or other optical arrangement and images are taken at periodic intervals for between about 1 hour to about 24 hours, and saved on computer or other electronic storage media. It will be understood by those of ordinary skill that the type of microscopic imaging equipment can vary and can include any known systems or apparatus which can image cells using any type of electromagnetic radiation. Imaging systems include, but are not limited to, phase contrast, brightfield, differential interference contrast, fluorescence, and confocal microscopy and in-line holography.

Figure 17A:
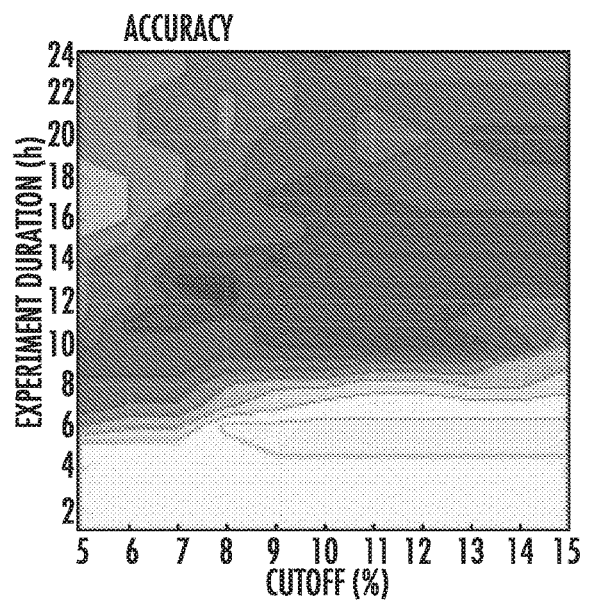
(FIG. 17A) Accuracy is defined as the percentage of classifications correctly predicted by the cutoff compared to those listed in FIG. 8. The highest accuracy value was 96%, and was observed for a cutoff of 7% and a duration of 12 hours, and also for a cutoff of 8% and a duration of either 12 hours or 13 hours.
Figure 17B:
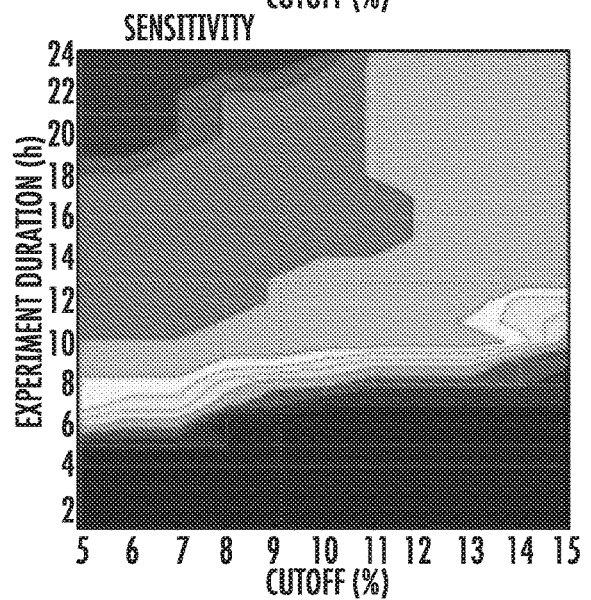
(FIG. 17B) Sensitivity is defined as the percentage of metastatic cell lines listed in FIG. 8 that were predicted to be metastatic by the cutoff. The maximum sensitivity observed was 100%, which occurs for cutoff values of or below 10%, and experiment durations equal to or greater than 19 hours.
Figure 17C:
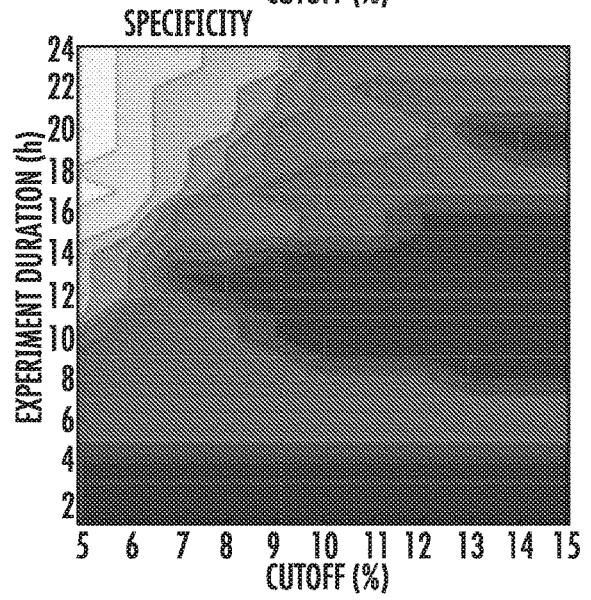
(FIG. 17C) Specificity is defined as the percentage of non-metastatic cell lines listed in FIG. 8 that were predicted to be non-metastatic by the cutoff. The maximum specificity value observed was 100%, which was observed for a wide range of conditions. Importantly, the cutoff and duration values that gave the maximum accuracy coincided with a high sensitivity value of 90% and a maximum specificity value of 100%.

As used herein the "period of time" that the cells can be imaged using the apparatus and methods of the present invention can vary. In some embodiments the cells can be imaged for 1 or more hours, or in some embodiments about 6 or more hours, in some embodiments, 12 or more hours, and in some embodiments between 12 and 24 hours. It is possible to run the methods with device for a longer duration, however, with longer duration there is an increasing likelihood that cells from non-metastatic cell lines will eventually make it into the bifurcation (increasing the likelihood for a false positive result). For the lower limit, a period of time needs to elapse so the cells have time to migrate in the device. Based on the experimental data shown in FIG. 17 and Example 10, 6 hours is the earliest time point where accuracy begins to increase.

In accordance with one or more embodiments, the operation of the apparatus and methods of the present invention can be performed without the need of external pumps or valves, and the function is driven by gravity and the topography of the channels in the apparatus. However, it is contemplated that alternative embodiments of the invention could encompass external pumps or valves depending on the function desired, and is well within the ability of the skilled artisan.

In a preferred embodiment, the apparatus and methods of the present invention include methods for prognostic purposes in which migration of cancer cells to one of the bifurcation branches of the migration channels is associated with a disease state. In this embodiment, migration in the device serves as a companion diagnostic with other methods of cancer diagnosis. A high migration score indicates that the specific cancer tested has a high propensity to metastasize and indicates that aggressive treatment should be undertaken.

In accordance with an embodiment, the inventive methods can be used to predict survivability of a subject with a brain tumor. For example, a subject diagnosed with a brain tumor using known means can undergo either a biopsy of the tumor or complete surgical resection of the tumor, or a portion thereof. One or more cells from the tumor or biopsy are then suspended in suitable growth media. A sample or aliquot of a sufficient number of cells are then added to the microfluidic device as described herein. The cells are then imaged over time and the images are observed to determine if any of the cells in the sample have moved from the cell inlet reservoir (11) to the migratory channel (14). If any of the cells in a defined period of time have migrated to the bifurcation point of the migratory channel (14) or the cells have migrated into the two or more outlet ends (16), or exited out of the outlet ends, then those cells are defined as being invasive.

As used herein, the term "invasive" refers to a cell or population of cells from a tumor of the subject that display the migratory behavior of migrating into the cell migratory channel (14) of the integrated microfluidic apparatus and migrating past the bifurcation point of the migratory channel (14) or the cells have migrated into the two or more outlet ends (16), or exited out of the outlet ends. The inventors have experimental data from brain cancer patients that show that tumors with invasive cells are highly correlated with low survivability and high risk of recurrence (FIG. 11). Without being limited to any particular theory, it is contemplated that these invasive cell subpopulations are tumor or cancer stem cells and highly migratory in vivo.

In accordance with an embodiment, the present invention provides a method for identifying the invasiveness of a cancer cell or population of cells in a sample comprising: a) obtaining a cell or population of cancer cells from the sample of a tumor; b) incubating the cells for a period time in a integrative microfluidic apparatus; c) imaging the cells in the apparatus for a period of time; and d) determining whether a cell or subpopulation of cells in the sample are invasive.

In accordance with an embodiment, the present invention provides a method for predicting and/or prognosing the survival and/or recurrence of a patient having a tumor, comprising: a) obtaining a cell or population of cells from the tumor of a patient; b) adding a sufficient sample of the cells from the tumor to an integrated microfluidic apparatus; c) incubating the cells for a period time in a integrative microfluidic apparatus; d) imaging the cells in the integrated microfluidic apparatus for a period of time; e) determining whether a cell or subpopulation of cells in the sample are invasive; and; g) identifying the tumor of the subject as having low survivability or a high risk of recurrence when the proportion of invasive cells is greater than a cutoff range of the migratory cells.

In accordance with an embodiment, the present invention provides a method for predicting and/or prognosing patient survival and/or recurrence for patients having a tumor comprising: a) obtaining a cell or population of cells from the tumor of a patient; b) adding a sufficient sample of the cells from the tumor to an integrated microfluidic apparatus; c) incubating the cells for a period time in a integrative microfluidic apparatus; d) imaging the cells in the integrated microfluidic apparatus for a period of time; e) determining whether a cell or subpopulation of cells in the sample are invasive; and; g) identifying the tumor of the subject as having low survivability or a high risk of recurrence when the proportion of invasive cells is greater than 5% to about 50%, or in some embodiments, between about 5% to about 40% of the migratory cells, or in some embodiments, between about 10% to about 25% of the migratory cells.

In accordance with another embodiment, the present invention provides a method for predicting and/or prognosing a brain tumor patient survival and/or recurrence comprising: a) obtaining a cell or population of cells from the tumor of a patient; b) adding a sufficient sample of the cells from the tumor to the integrated microfluidic apparatus; c) imaging the cells in the integrated microfluidic apparatus for a period of time; d) comparing the images of the cells in the integrated microfluidic apparatus over time; e) determining the number of cells or subpopulation of cells which migrate past the bifurcation of any of the migratory channels of the apparatus into either of the one or more outlet ends of the migration channels of the integrated microfluidic apparatus and/or exits out of the outlet ends of the migration channels; f) identifying the tumor as having low survivability or a high risk of recurrence when the proportion of cells entering through either the wide or narrow outlet ends of the integrated microfluidic apparatus is greater than 5% to about 50%, of all cells, or in some embodiments, 5% to about 40% of all cells, or in some embodiments, between about 10% to about 25% of all cells.

It will be understood by those of ordinary skill in the art that the exact steps for using the integrated microfluidic apparatus to determine invasiveness of tumor cells from a sample can be varied from the methods described above. Samples can be placed in the apparatus after media has been added, and with or without addition of chemotherapeutic or other biologically active agents. The dimensions of the apparatus can also be altered without changing the overall operation of the microfluidic apparatus.

In some percentage of the samples from brain cancer patients, the migratory or invasive cells migrated into one or the other outlet ends. The inventors noted that the proportion of cells which migrated through the narrower of the two outlet ends (3 μm) also correlated with three-fold less survival time in patients. Moreover, in populations of cells that were migratory in a sample, there was a highly significant correlation between the proportion of migratory cells that enter the narrow outlet end or wide outlet end and survival times as well. Patients with tumor cell samples having 85% or more wide outlet end migratory cells having greater than two or three-fold survival times over those having less than 85%.

Figure 2A:
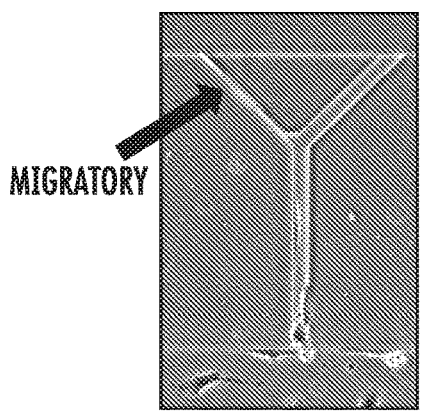
FIG. 2 illustrates the migration of migratory and non-migratory MDA-MB-231 cells within the device. (2A) Representative image of migratory cell in 3 µm-wide branch channel. (2B) Representative image of non-migratory cell within base channel of device. Migratory cells moved within the microchannels with significantly greater average speed (2C) and chemotactic index or persistence (2D). (2E) Ellipses fit to the cell outlines had major axes highly aligned with the base channel in 89% of the migratory cells but only 52% of the non-migratory cells. (2F) Migratory cells were significantly more elongated than non-migratory cells, as measured by the circularity of the cell outline. *, $p<0.05$.
Figure 2B:
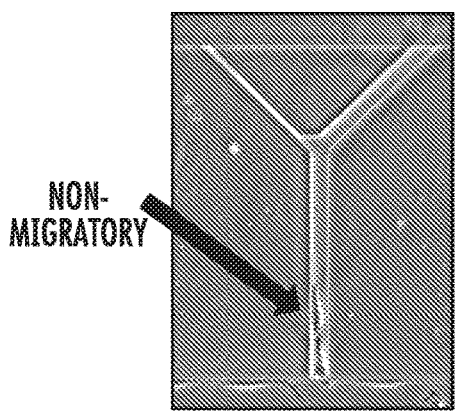

It is also contemplated that the apparatus of the present invention can be used to isolate or separate a cell or subpopulation of cells from a collection of cells in a sample. In accordance with an embodiment, cells can be separated from the integrated microfluidic apparatus by means of trypsinization or chelation, which allows the cells to detach from the channel walls. For example, trypsin or EDTA can be introduced into all of the inlet reservoirs. The cells detach and the flow of the integrated microfluidic apparatus is such that the cells that have migrated through the migratory channels will flow through the first channel and move into the upper outlet reservoir (FIG. 2A).

In some embodiments, the migratory cells may be isolated from the integrated microfluidic apparatus and subjected to genomic or proteomic analysis. Such analysis includes, but is not limited to, analysis of gene expression levels using quantitative real-time polymerase chain reaction, RNA sequencing, and surface protein expression levels using flow cytometry.

In accordance with an embodiment of the present invention, it will be understood that the term "biological sample" or "biological fluid" includes, but is not limited to, any quantity of cells from a living or formerly living subject. Such cells include, but are not limited to, blood, bone, bone marrow, T-cells, B-cells, fibroblasts, chondrocytes, synovial macrophages, endothelial cells, tumor associated cells, and skin cells.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The solid substrate used to make the integrated microfluidic apparatus of the present invention may be any suitable material. Representative examples of substrates include glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon and modified silicon including PDMS, carbon, metals, inorganic glasses and plastics. In a preferred embodiment, the material used in the substrate is modified silicon.

In some embodiments, the integrated microfluidic apparatus and methods used are methods of diagnosis and the migration of cells is associated with a diseased state. In one preferred embodiment, the migration of cells is associated with cancer, such as solid tumors. In particular, cancers such as brain cancers like glioblastoma multiforme, prostate cancer, melanoma, bladder cancer, breast cancer, lymphoma, ovarian cancer, lung cancer, colorectal cancer or head and neck cancer. In other preferred embodiments, migration of cells is associated with an immunological disorder; inflammation; rheumatoid arthritis; cystic fibrosis; or an infection, for example, a viral or bacterial infection. In other embodiments, the apparatus and methods used are methods of monitoring prognosis and the migration of cells is associated with the prognosis of a disease.

In yet another embodiment, the integrated microfluidic apparatus and methods used are for monitoring drug treatment and the migration of cells is associated with the drug treatment. In particular, the apparatus and methods used are (e.g., analysis of migration of cells) for the selection of population-oriented drug treatments and/or in prospective studies for selection of dosing, for activity monitoring and/or for determining efficacy endpoints. In this embodiment, decreased migration upon application of a particular biologically active molecule indicates that that molecule effectively inhibits the movement of migratory or invasive cells.

The diagnosis can be carried out in a person with or thought to have a disease or condition. The diagnosis can also be carried out in a person thought to be at risk for a disease or condition. "A person at risk" is one that has either a genetic predisposition to have the disease or condition or is one that has been exposed to a factor that could increase his/her risk of developing the disease or condition.

Therefore, in accordance with an embodiment, the present invention provides a method for identifying an agent which inhibits the invasiveness of a cell or population of tumor cells in a sample comprising: a) adding to the integrated microfluidic apparatus an a cell or population of cells from the sample and the test agent; b) incubating the cells for a period time; c) imaging the cells in the apparatus for a period of time; d) comparing the images of the cells in the integrated microfluidic apparatus over time; e) identifying a cell or subpopulation of cells in the sample as invasive when the cell or subpopulation of cells migrates past the bifurcation of any of the migratory channels of the apparatus into either of the one or more outlet ends of the migration channels of the integrated microfluidic apparatus and/or exits out of the migration channels; f) comparing the number and/or extent of invasiveness of the cell or subpopulation of cells to the number and/or extent of migration of the cell or subpopulation of cells of e) to the number and/or extent of migration of a control cell or subpopulation of cells migrating in the absence of the agent.

In accordance with another embodiment, the present invention provides a method for identifying an agent which inhibits the invasiveness of a cell or population of brain tumor cells in a sample comprising: a) adding to the inlet reservoir of the second channel of the integrated microfluidic apparatus an aliquot of a suspension of a population of cells from the sample and the test agent; b) incubating the cells for a period time to allow the cells to fill the second channel; c) removing any remaining cell suspension from the reservoir of the second channel and washing the inlet of the second channel; d) adding cell media containing the molecule to the one or more reservoirs of the one or more inlets of the first channel; e) imaging the cells in the apparatus for a period of time; f) comparing the images of the cells in the integrated microfluidic apparatus over time and identifying a cell or subpopulation of cells in the sample as invasive when the cell or subpopulation of cells migrates past the bifurcation of any of the migratory channels of the apparatus into either of the one or more outlet ends of the migration channels of the integrated microfluidic apparatus and/or exits out of the migration channels; g) comparing the number and/or extent of invasiveness of the cell or subpopulation of cells to the number and/or extent of migration of the cell or subpopulation of cells of f) to the number and/or extent of migration of a control cell or subpopulation of cells migrating in the absence of the agent.

Detection of cancers at an early stage is crucial for its efficient treatment. Despite advances in diagnostic technologies, many cases of cancer are not diagnosed and treated until the malignant cells have invaded the surrounding tissue or metastasized throughout the body. Although current diagnostic approaches have significantly contributed to the detection of cancer, they still present problems in sensitivity and specificity.

In accordance with one or more embodiments of the present invention, it will be understood that the types of cancer diagnosis which may be made, using the integrated microfluidic apparatus and methods provided herein, is not necessarily limited. For purposes herein, the cancer can be any cancer. As used herein, the term "cancer" is meant any malignant growth or tumor caused by abnormal and uncontrolled cell division that may spread to other parts of the body through the lymphatic system or the blood stream.

The cancer can be a metastatic cancer or a non-metastatic (e.g., localized) cancer. As used herein, the term "metastatic cancer" refers to a cancer in which cells of the cancer have metastasized, e.g., the cancer is characterized by metastasis of a cancer cells. The metastasis can be regional metastasis or distant metastasis, as described herein.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive apparatus and methods can provide any amount of any level of diagnosis, staging, screening, or other patient management, including treatment or prevention of cancer in a mammal.

In accordance with an embodiment, the methods disclosed herein can be used to assess the likelihood of survival and median survival times of patients having brain tumors. In a preferred embodiment, the brain tumor is a glioblastoma. The methods disclosed herein can be used to predict or prognose the survival time of a patient after undergoing a biopsy or resection of the tumor. The information is useful to inform the patient as to the status of the cancer. For example, a patient who is diagnosed as having a tumor with a large number of invasive cells, or a greater proportion of cells that enter the wide or narrow exit channels, based on the methods described herein, would be informed of the lower that average survival time expected. This information can be used by the patient to determine whether any treatment should be undertaken, or whether a modest or aggressive course of treatment is warranted, depending on the needs of the patient.

It will also be understood by those of skill in the art, that highly invasive cells identified using the apparatus and methods disclosed herein, are expected to be more resistant to treatment and have a higher than average risk of recurrence, even after surgery and chemotherapeutic or other treatments are undertaken.

In accordance with the inventive integrated microfluidic apparatus and methods, the terms "cancers" or "tumors" also include but are not limited to adrenal gland cancer, biliary tract cancer; bladder cancer, brain cancer; glioblastoma, breast cancer; cervical cancer; choriocarcinoma; colon cancer; endometrial cancer; esophageal cancer; extrahepatic bile duct cancer; gastric cancer; head and neck cancer; intraepithelial neoplasms; kidney cancer; leukemia; lymphomas; liver cancer; lung cancer (e.g. small cell and non-small cell); melanoma; multiple myeloma; neuroblastomas; oral cancer; ovarian cancer; pancreas cancer; prostate cancer; rectal cancer; sarcomas; skin cancer; small intestine cancer; testicular cancer; thyroid cancer; uterine cancer; urethral cancer and renal cancer, as well as other carcinomas and sarcomas.

An "active agent or molecule" and a "biologically active agent or molecule" are used interchangeably herein to refer to a chemical or biological compound that induces a desired pharmacological and/or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent," "pharmacologically active agent" and "drug" are used, then, it is to be understood that the invention includes the active agent per se as well as pharmaceutically acceptable, pharmacologically active salts, esters, amides, prodrugs, metabolites, analogs etc.

As used herein, biologically active molecules which can be introduced into the apparatus and used in the methods disclosed herein include, but are not limited to, dyes, including fluorescent, and NIRF dyes, enzymes, and enzyme linked dyes and markers, receptor antagonists or agonists, hormones, growth factors, autogenous bone marrow, antibiotics, antimicrobial agents, and antibodies. Non-limiting examples of biologically active agents include following: adrenergic blocking agents, anabolic agents, androgenic steroids, antacids, anti-asthmatic agents, anti-allergenic materials, anti-cholesterolemic and anti-lipid agents, anticholinergics and sympathomimetics, anti-coagulants, anti-convulsants, anti-diarrheal, anti-emetics, anti-hypertensive agents, anti-infective agents, anti-inflammatory agents such as steroids, non-steroidal anti-inflammatory agents, anti-malarials, anti-manic agents, anti-nauseants, anti-neoplastic agents, anti-obesity agents, anti-parkinsonian agents, anti-pyretic and analgesic agents, anti-spasmodic agents, anti-thrombotic agents, anti-uricemic agents, anti-anginal agents, antihistamines, anti-tussives, appetite suppressants, benzophenanthridine alkaloids, biologicals, cardioactive agents, cerebral dilators, coronary dilators, decongestants, diuretics, diagnostic agents, erythropoietic agents, estrogens, expectorants, gastrointestinal sedatives, agents, hyperglycemic agents, hypnotics, hypoglycemic agents, ion exchange resins, laxatives, mineral supplements, mitotics, mucolytic agents, growth factors, neuromuscular drugs, nutritional substances, peripheral vasodilators, progestational agents, prostaglandins, psychic energizers, psychotropics, sedatives, stimulants, thyroid and anti-thyroid agents, tranquilizers, uterine relaxants, vitamins, antigenic materials, and prodrugs.

When the biologically active molecule is a dye, the molecule is detected by fluorescence imaging. The dyes may be emitters in the visible or near-infrared (NIR) spectrum. Known dyes useful in the present invention include carbocyanine, indocarbocyanine, oxacarbocyanine, thuicarbocyanine and merocyanine, polymethine, coumarine, rhodamine, xanthene, fluorescein, boron-dipyrromethane (BODIPY), Cy5, Cy5.5, Cy7, VivoTag-680, VivoTag-S680, VivoTag-S750, AlexaFluor660, AlexaFluor680, AlexaFluor700, AlexaFluor750, AlexaFluor790, Dy677, Dy676, Dy682, Dy752, Dy780, DyLight547, Dylight647, HiLyte Fluor 647, HiLyte Fluor 680, HiLyte Fluor 750, IRDye 800CW, IRDye 800RS, IRDye 700DX, ADS780WS, ADS830WS, and ADS832WS.

The term "modulate," as used herein means that in the presence of the biologically active agent or molecule, the migratory ability of the cell or subpopulation of cells is up regulated or down regulated, such that migration level, or activity is greater than or less than that observed when compared to controls. For example, the term "modulate" can mean "inhibit," but the use of the word "modulate" is not limited to this definition.

The term "inhibit" as used herein, means that that in the presence of the biologically active agent or molecule, the migratory ability of the cell or subpopulation of cells is lowered or down regulated when compared to controls.

EXAMPLES

Fabrication of an embodiment of the apparatus of the present invention: The microfluidic device consisted of "Y"-shaped microchannels, with a 20 µm-wide feeder channel bifurcating to 20 µm-wide or 3 µm-wide branches, arrayed between mutually perpendicular cell seeding and cell outlet channels. Microchannels were of height $H_C=10$ µm and length $L_C=200$-400 µm and were spaced 50 µm apart.

The apparatus was fabricated using multilayer photolithography and replica molding. Photolithography masks were designed using AutoCAD (Autodesk, McLean, Va.) and produced by the Photoplot Store (Colorado Springs, Colo.). The master for the device contained a negative mold of the final device and was fabricated using SU-8 3010 positive photoresist (Microchem, Newton, Mass.). SU-8 3010 was spin coated (Single Wafer Spin Processor, Model WS-400A-6NPP-LITE, Laurell Technologies, North Wales, Pa.) on a cleaned silicon wafer (University Wafer, South Boston, Mass.) to create a 10 µm-thick film. The film was soft baked on a hot plate and exposed to 170 mJ/cm2 of UV light energy through the chrome-on-glass light field mask using an EVG620 mask aligner (EVG, Austria) to define the microchannels. The wafer was baked, post-exposure, to cross link the pattern before development with SU-8 developer. Following development, a 50 µm-thick SU-8 3025 film was spun onto the wafer and soft baked. A mask defining the medium feed lines was aligned with the channels, and the photoresist was exposed to 250 mJ/cm2 of energy. The final master was developed, hard baked, and passivated with a fluorinated silane [(tridecafluoro-1,1,2,2-tetrahydrooctyl)-1-trichlorosilane] (Pfaltz & Bauer, Waterbury, Conn.) overnight in a vacuum desiccator.

Completed devices were molded from the SU-8 masters by pouring polydimethylsiloxane (PDMS) (Sylgard® 184 Silicone Elastomer Kit, Dow Corning, Midland, Mich.) at a 10:1 ratio of prepolymer:crosslinker over the master, degassing, and curing at 85° C. for 2 hours. Devices were diced, and 6-mm inlet and outlet ports were punched in the PDMS fluid layer. The devices and glass coverslips were cleaned with ethanol and DI water and plasma treated for 2 minutes at 18 W (Harrick PDC-32G, Harrick Plasma, Ithaca, N.Y.). The device was bonded to the glass slide and coated with 20 µg/ml rat tail collagen type I (BD, Franklin Lakes, N.J., USA) for 1 hour at 37° C. Following coating, the channels were washed with DPBS to prepare for cell seeding.

Description of an embodiment of the apparatus used in the examples of the present invention. The apparatus, termed a "Microchannel Migration Device," comprises a plurality of Y-shaped microchannels arrayed between cell seeding (second channel) and medium (first channel) lines (FIG. 1A). The microchannels were designed such that 20 µm base channels bifurcated to 20 µm and 3 µm branch channels at a 45° or 65° (from the horizontal) angle (inset, FIG. 1A). With this device design, experiments can be carried out with or without a chemoattractant gradient. If no gradient is desired, growth medium is placed in all four inlet wells, and the topography of the channels is the only driver of migration. When medium containing a chemoattractant is placed in the uppermost medium inlet well and medium without chemoattractant is placed in the cell inlet and bottom two medium inlet wells, a gradient is formed within the microchannels to induce migration.

Figure 1C:
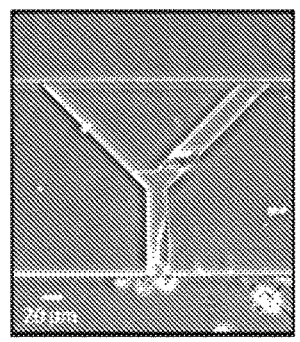
Figure 1D:
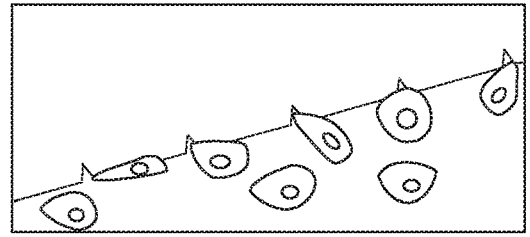

The particular embodiment of the device was formed by bonding a PDMS mold containing the microchannels and medium channels to a glass coverslip (FIG. 1B). Cells were seeded at the bases of the microchannels following gravity-driven flow of suspended cells from the cell inlet well (shown schematically in FIG. 1C). Medium was placed in all inlet wells following cell seeding. Importantly, cell seeding and migration were carried out without the need for external pumps or valves, and all flow was driven by gravity. Seeded cells migrated through the channels over the course of the experiment (FIG. 1D).

Cell seeding and live cell migration experiments: Cells were grown to confluency, trypsinized, and resuspended in serum-free medium at $2 \times 10^6$ cells/ml. 50 µl of cell suspension was added to the cell inlet well. Cells were incubated in the device for 5-10 minutes at 37° C. to allow initial cell seeding at the base of "Y" channels. The cell suspension was then removed from the cell inlet port. The device was washed with DPBS before the addition of medium to the inlet ports of the device. In select experiments, PI3K activity was inhibited by the addition of 10 µM LY294002 in the medium through the entire course of migration. The migration chamber was moved to a temperature- and $CO_2$-controlled stage-top live cell incubator (Okolab, Italy) mounted on the motorized stage of an inverted Nikon Eclipse Ti microscope (Nikon, Tokyo, Japan) with automated controls (NIS-Elements, Nikon). Migrating cells were imaged with a 10×-magnification phase contrast objective every 10 minutes for up to 16 hours.

Analysis of Cell Migration: Video files were exported to ImageJ for analysis. All cells that entered the channel were tracked while fully inside the channel and before reaching either end of the channel using the ImageJ MTrackJ plugin at 10 minute intervals. Cells were also dynamically traced with the ImageJ polygon ROI capability at 30 minute intervals. Dividing cells were not tracked.

Cell position data were used to calculate cell speed over each 10 minute interval, and these speeds were averaged to get an overall average speed for each cell. Additionally, the chemotactic index, defined as the cell displacement divided by the total distance travelled by the cell, was calculated. Cell shape data were used to calculate cell circularity and fit elliptical angle using the Measure function in ImageJ. Statistical significance was assessed with non-paired Student's t-test.

Cells were further defined as migratory or non-migratory. Migratory cells were defined as those cells which reached the bifurcation in the Y-shaped microchannel; all other cells were defined as non-migratory. Migratory cells were then classified as contact guided or not contact guided. Cells were defined as contact guided if they continued to the branch channel on the side of the base channel on which they were migrating when the bifurcation was reached. Cells that switched walls in the bifurcation region were classified as not contact guided.

Isolation of Migratory Cells: Cells that had migrated through and exited the channels were washed with a chelator (versene) prior to the addition of 0.25% trypsin to all inlet wells of the device. Hydrodynamic resistance to flow in the narrow microchannels prevented the backflow of cells that had migrated through the microchannels back into the microchannels. Detached cells flowed to the upper outlet well, were collected in culture medium, and were plated in 96-well plates for expansion. Expanded cells were analyzed for the presence of tumor stem cell markers (for example, CD44 or CD271).

Alternatively, ~300 migratory cells were collected, suspended in 75 µl of DPBS, mixed with 75 µl of Matrigel, and injected to the mammary fat pad of an immunodeficient mouse. An equal number of control cells that had not migrated through the microchannels were collected and injected in an identical manner. Mice were sacrificed 8 weeks post-injection, and the lungs were histologically analyzed to detect metastases.

Example 1

Figure 2C:
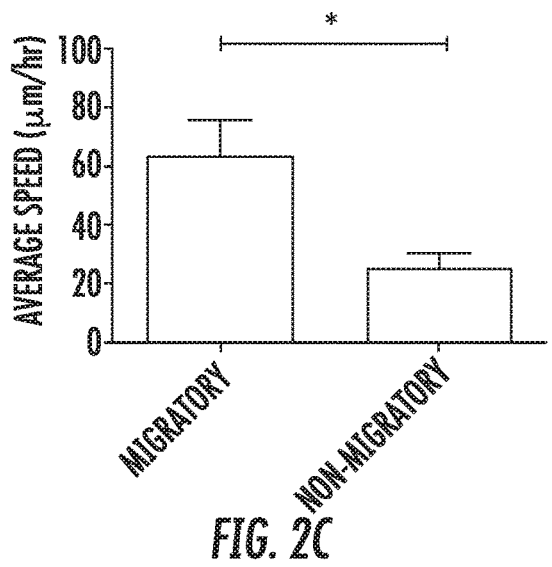
Figure 2D:
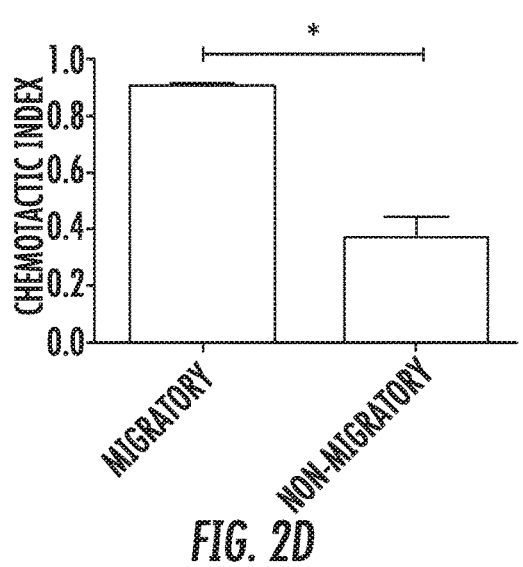

Bifurcating Channels Allow Identification of Migratory Cells: Cell tracking of all MDA-MB-231 cells within the channels revealed two distinct subpopulations: migratory and non-migratory cells (FIGS. 2A,B). 22±3% of human metastatic MDA-MB-231 breast cancer cells were migratory. Interestingly, this subpopulation correlates with the % of MDA-MB-231 (28%) bearing the $CD44^+/CD24^-$ molecular signature[5] that is used to define breast cancer stem cells. Migratory cells, defined as those cells reaching the branch channels, migrated more than twice as fast as non-migratory cells (FIG. 2C). Migratory cells were also significantly more directional. The chemotactic index of migratory cells increased to 0.91 in comparison to a chemotactic index of 0.37 for nonmigratory cells.

Figure 2E:
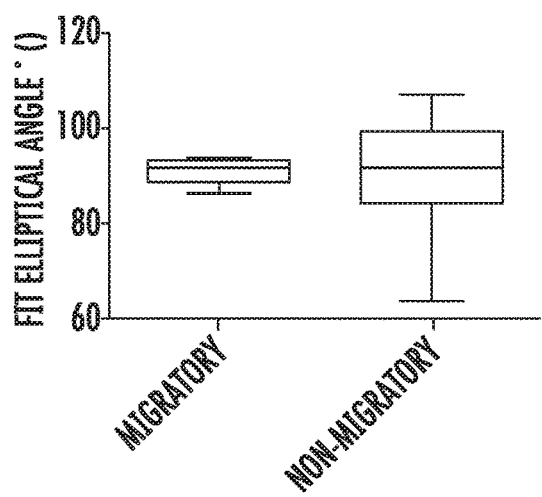
Figure 2F:
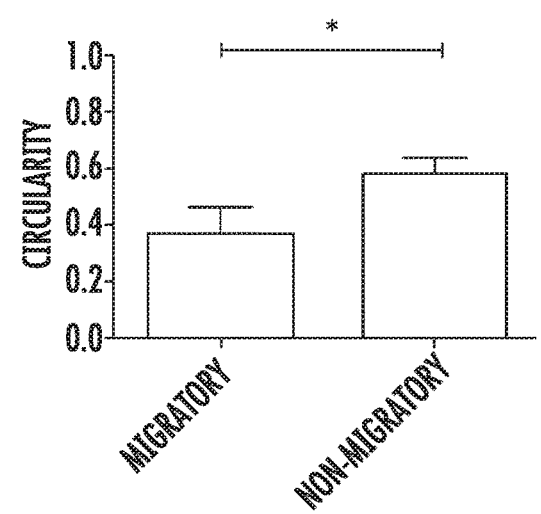

Analysis of cell shape indicated that migratory cells were aligned with and elongated along the channel wall. The fit elliptical angle of a cell perfectly aligned along the wall was 90°. Although both migratory and non-migratory cells had an average fit elliptical angle of 90°, 89% of migratory cells had fit elliptical angles within 10° of 90°, while only 52% of non-migratory cells showed this high degree of alignment (FIG. 2E). This directed migration was confirmed by analysis of migration in the base channel. In that region of the microchannel, migratory cells changed direction an average of 0.6 times, while non-migratory cells averaged 5.6 direction changes. Circularity, a shape factor that decreases as shapes become less circular, was also significantly different between migratory and non-migratory cells. Migratory cells were significantly more elongated as they migrated, with a circularity of 0.37. Non-migratory cells had an average circularity of 0.58 (FIG. 2F). Additionally, the apparatus of the present invention was used for analysis of cytoskeletal components and intracellular signals via fluorescence microscopy (FIG. 3). This was possible because the device was constructed of transparent materials. Migratory cells showed increased localization of F-actin to the cell leading edge (FIG. 3A,D). Actin localization was not seen in non-migratory cells (rounded cell at base of channel, FIG. 3D). Similarly, the Rho GTPases Rac1 and Cdc42 were polarized in migratory cells, particularly when these cells reached the 3 µm-wide branch channel (FIG. 3B,C,E,F). Non-migratory cells did not exhibit this polarization (for example, cell at channel base in FIG. 3B).

Example 2

Figure 4A:
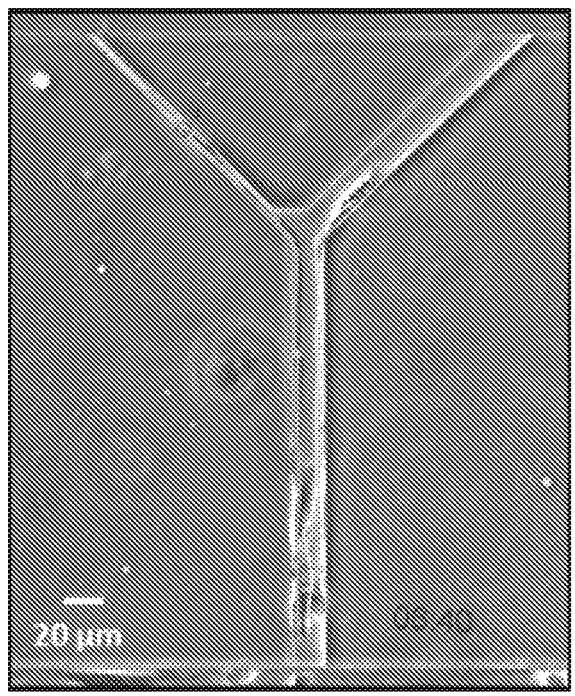
FIG. 4 depicts how migratory MDA-MB-231 cells are contact guided at the microchannel bifurcation. (4A) Representative cell tracks of migratory cells. Cells migrate predominantly up one channel wall and continue to follow that wall at the bifurcation as they enter a branch channel. (4B) Percentage of migratory cells that were contact guided to the 3 μm-wide and 20 μm-wide branches.
Figure 4B:
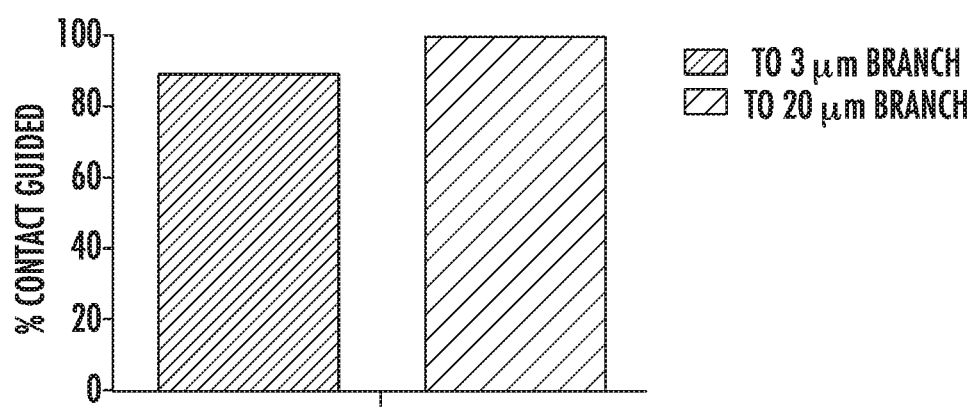

Contact Guidance Overcomes Steric Hindrance for Migratory Cells: Of those cells that were migratory, the vast majority moved preferentially along one wall of the feeder channels and remaining polarized, with a significantly lower number of changes in direction compared to non-migratory cells. Representative cell tracks illustrating this trend are shown in FIG. 4A. Interestingly, migration direction at the bifurcation was not dependent on the width of the resultant branch, even though entering the 3 µm-wide branch required significant deformation of the cell body. Instead, cells continued to be polarized and moved readily into the "branch" channel, regardless of the branch channel width (FIG. 4B). Thus, contact guidance dominated steric hindrance at these channel widths for migratory cells and was likely the driver of directed migration for this subpopulation.

Example 3

PI3K Inhibition Promotes Spontaneous Migration of MDA-MB-231 Cells: There is evidence that PI3K signaling is required to stabilize nascent protrusions. New protrusions away from the wall along which a cell is migrating would discourage contact guidance. Therefore, it was investigated whether inhibiting PI3K could promote contact guidance in 200 µm-long microchannels.

Figure 5A:
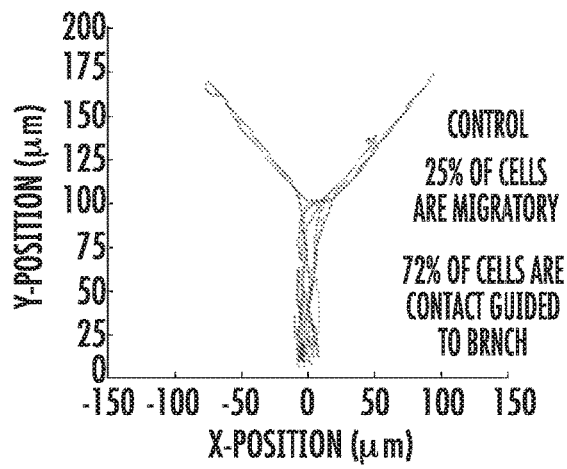
FIG. 5 illustrates that PI3K inhibition promotes MDA-MB-231 cell migration and contact guidance within the microchannels. Representative tracks of (5A) control and (5B) PI3K inhibited cells migrating within 200 μm-long microchannels. PI3K inhibition with 10 μM LY294002 increased the percentage of cells that were migratory and that were contact guided. (5C) The average speed of control and LY294002-treated cells was the same. (5D) The chemotactic index of LY294002-treated cells was greater than that of control cells.
Figure 5B:
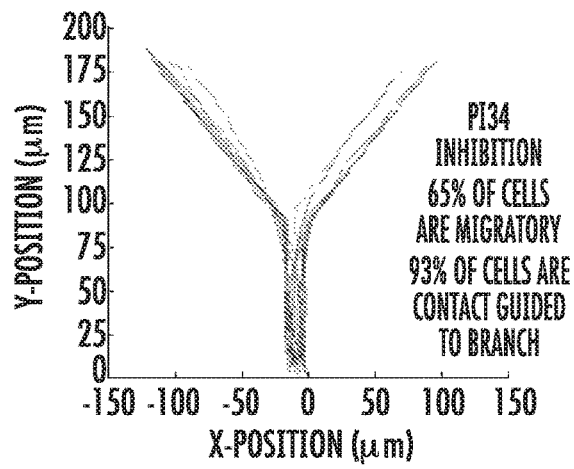
Figure 5C:
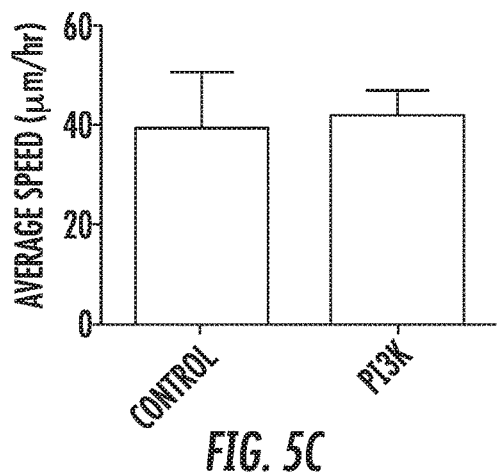
Figure 5D:
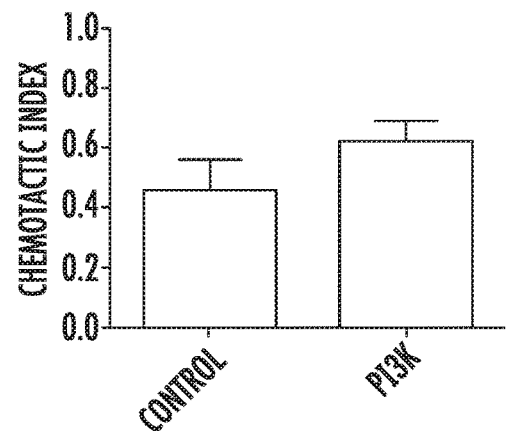

Inhibition of PI3K signaling using the PI3K inhibitor LY294002 increased the migratory cell population in 200 µm-long microchannels from 25% to 65% and the ratio of contact guided cells from 66% to 93% (FIG. 4A,B). PI3K inhibition did not impact overall cell speed, as control and LY294002-treated cells moved at the same average speed (FIG. 5C). However, cells in which PI3K signaling was inhibited moved with greater directionality, as indicated by the higher chemotactic index for these cells vs. control cells (FIG. 5D). This result is consistent with the expected inhibition of nascent protrusions upon LY294002 treatment, as new protrusions would be required for the cell to change direction.

Example 4

Device Design Allows Isolation of Migratory Cells: Further characterization of migratory and non-migratory cells will provide important information on the nature of these cell populations. For example, we wish to characterize whether migratory cells show stem-like characteristics, retain high migratory potential over several generations, or display differential gene expression in comparison to non-migratory cells. To answer these questions, it will be necessary to isolate migratory cells from the device.

Proof-of-concept experiments were performed to isolate migratory cells. A375 cells migrated through straight microchannels toward a chemotactic cue. Trypsin was added to all inlet wells of the device and caused the migratory cells to become detached and flow to the upper medium outlet well (FIG. 6A). Resistance to flow through the narrow microchannels prevented detached cells from flowing back into the microchannels. Migratory cells were collected in the upper medium outlet well (FIG. 6B) and plated in 96-well plates for expansion. Expanded cells were analyzed for expression of the cancer stem cell marker CD271 using flow cytometry. Migratory A375 cells displayed increased expression of this marker compared to cell populations from which the migratory subpopulation had not been extracted (FIG. 6C).

Example 5

Figure 7A:
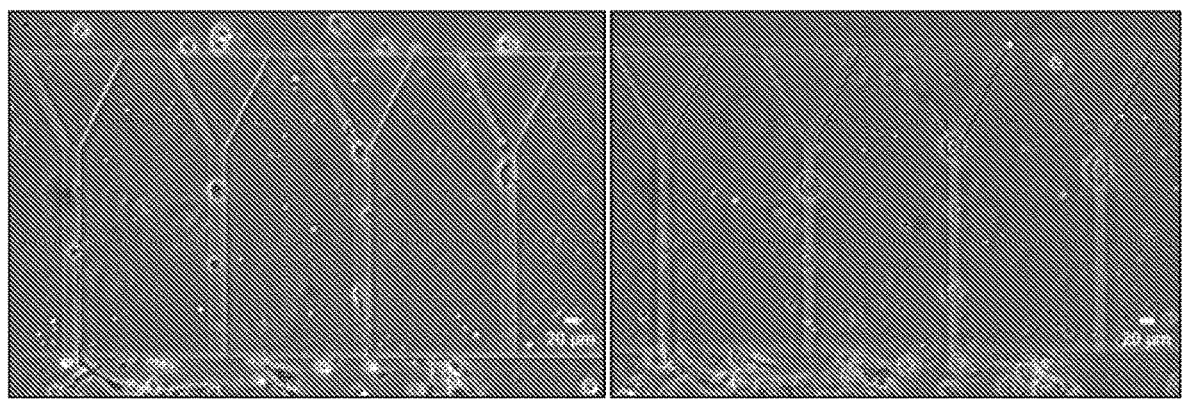
FIG. 7 depicts the isolation of migration MDA-MB-231 cells from a migration device of the present invention. (7A) Migratory cells that exited the microchannels are shown prior to (left panel) and following (right panel) extraction from the device. Note that the position of the nonmigratory cells and cells seeded at the entrances to the channels is the same before and after extraction of migratory cells. (7B) Orthotopic injection of migratory cells but not control cells to the mammary fat pad of immunodeficient mice resulted in the formation of metastases (arrows).
Figure 7B:
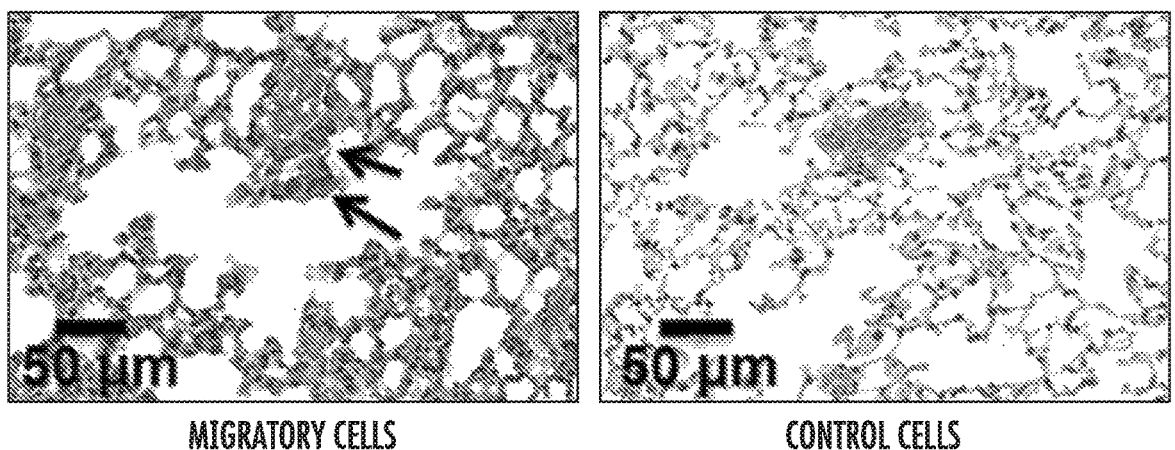

Migratory cells are more likely to cause metastasis upon orthotopic injection in immunodeficient mice: MDA-MB-231 cells migrated through the device in the absence of a chemotactic cue. Trypsin was added to the all medium inlet wells of the device and caused the migratory cells to become detached and flow to the upper medium outlet well (FIG. 7A). Resistance to flow through the narrow microchannels prevented detached cells from flowing back into the microchannels (FIG. 7A; compare cell positions in microchannels before and after removal of migratory cells). Approximately 300 migratory cells were collected in the upper medium outlet well. Trypsin was then added to the cell inlet well. Cells that had not entered the channels flowed to the lower outlet well and were collected. Approximately 300 of these control cells were collected. Migratory or control cells were suspended in 75 µl DPBS, mixed with 75 µl Matrigel, and injected to the mammary fat pad of immunodeficient mice. Mice were sacrificed at 8 weeks post-injection. Histological analysis of the lungs of these mice revealed that migratory cells caused lung metastasis, whereas control cells did not (FIG. 7B; arrows indicate metastases).

Example 6

Observations using metastatic MDA-MB-231 breast cancer cells were generalized. A panel of cell lines comprised of non-cancerous and non-metastatic (normal) breast epithelial cells, non-metastatic breast cancer cells, and metastatic breast cancer cells was assayed in devices containing 400 µm-long Y-shaped migration channels (FIG. 8). In normal breast epithelial cell lines, an average of 2.6% of migratory cells was observed, with the lowest percentage observed in HMLE Luc 26 cells (0.5±0.8%) and the highest percentage observed in 184A1 cells (5.7±8.0%). Similarly, in non-metastatic breast cancer cell lines, an average of 2.0% migratory cells was observed, with the lowest percentage value observed in four non-metastatic breast cancer cell lines: ZR75-1, MDA-MB-468, SkBr3, and BT-20 (0±0%) and the highest percentage observed in non-metastatic breast cancer MCF7-Luciferase cells (6.5±5.8%). Conversely, larger subpopulations of motile cells were found in metastatic cell lines. Metastatic cell lines displayed an average of 20% migratory cells, with a minimum percentage observed in metastatic SUM149 cells (1.2±1.0%) and a maximum observed in metastatic MDA-MB-231 circulating tumor cells (46%±18%). Examples include: metastatic K-Ras-overexpressing/obscurin-knockdown MCF10A cells (20%), metastatic Bt-549 breast cancer cells (18±3.5%), metastatic MDA-MB-436 breast cancer cells (8.7±0.5%), metastastic MDA-MB-231 breast cancer cells (17±5%), metastatic Hs578t breast cancer cells (16±2%), and metastatic A375 melanoma cells (38±7%). The 38±7% of migratory human A375 melanoma cells closely matches the % of A375 cells expressing the cancer stem cell marker CD271.

The inventors then determined a cutoff range for the percentage of migratory cells observed in a cell line that predicted whether a tested cell line is non-metastatic (if the percentage of migratory cells observed in a cell line was below the cutoff) or metastatic (if the percentage of migratory cells observed in a cell line was above the cutoff). A range of cutoff values from 5% to 15% was considered; this range was selected because it was between the average percentage of migratory cells observed in non-metastatic cell lines (2-2.6%) and metastatic cell lines (20%). For each cutoff value, the classification of each cell line predicted by the cutoff value was compared to the known classification of that cell line (listed in FIG. 8). The accuracy (defined as the percentage of classifications correctly predicted by the cutoff compared to those listed in FIG. 8) was calculated for each cutoff value. For cutoff values of 7-8%, the highest accuracy value was calculated (96%), so this range was chosen as the cutoff between non-migratory and migratory cell lines. For the cutoff range of 7-8%, the sensitivity of the device (defined as the percentage of metastatic cell lines listed in FIG. 8 that were predicted to be metastatic by the cutoff) was 90%, and the specificity (defined as the percentage of non-metastatic cell lines listed in FIG. 8 that were predicted to be non-metastatic by the cutoff) was 100%.

Example 7

Triple negative breast cancer cells display divergent responses to pharmaceutical agents: A panel of triple-negative breast cancer (TNBC) cell lines were assayed in devices containing 400 µm-long Y-shaped migration channels in the presence or absence of the PI3K inhibitor LY294002 (10 µM (FIG. 9). PI3K inhibition did not affect the percentage of migratory cells measured for MDA-MB-436 (13±7% migratory for control vs. 18±7% for treated) cells or Hs578t (20±7% migratory for control vs. 15±2% migratory for treated) cells. PI3K inhibition increased migration of MDA-MB-231 (22±3% for control vs. 34±8% for treated) cells. In contrast, PI3K inhibition reduced the migration of Bt549 (32±8% for control vs. 19±1% for treated) cells.

Example 8

Figure 10A:
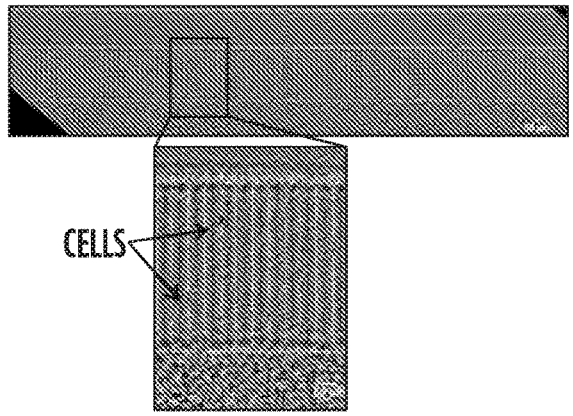
FIG. 10 depicts a representative sample of imaging techniques that can be used to assess migration in the present invention. (10A) Lens-free holography enables a wide field of view to be captured in a single image. Inset shows digitally zoomed image, with cells clearly visible in migration channels. (10B) Phase contrast microscopy (10× objective) image of migration channels with cells seeded at channel entrances. (10C) Combined phase contrast and fluorescence microscopy of cells within migration channels. A subset of cells was tagged with a fluorescent marker and appears green in the image.
Figure 10B:
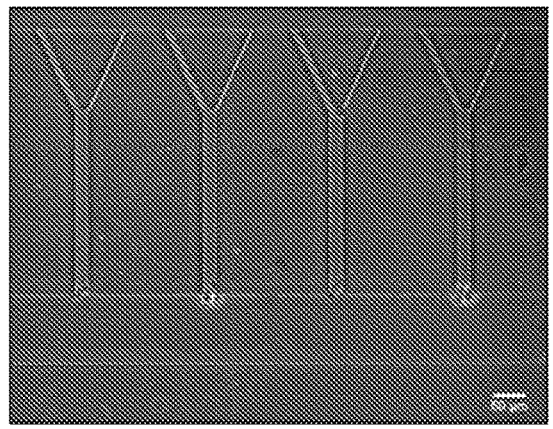
Figure 10C:
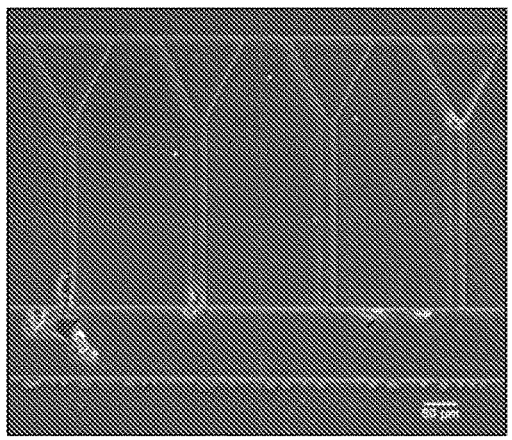
Figure 16B:
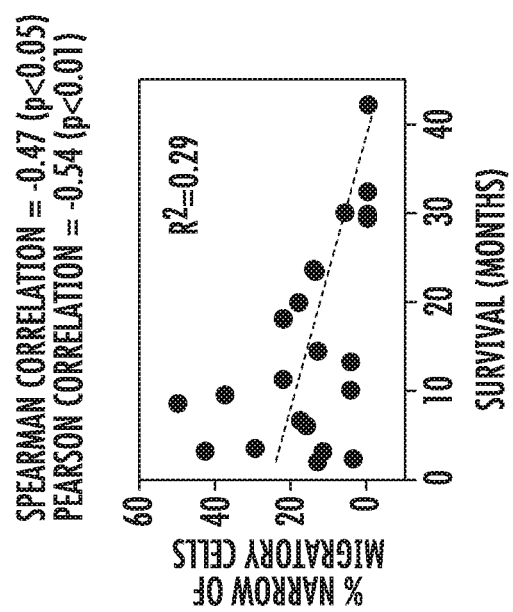
FIG. 16: Survival correlation—linear regression: (a) Linear regression analysis of % migratory and overall patient survival times (in months). Spearman and Pearson correlation analyses demonstrates significant negative correlation between the two variables. (b) Linear regression analysis of % narrow entry of migratory and overall patient survival times (in months). Spearman and Pearson correlation analyses demonstration significant negative correlation between the two variables.
Figure 16A:
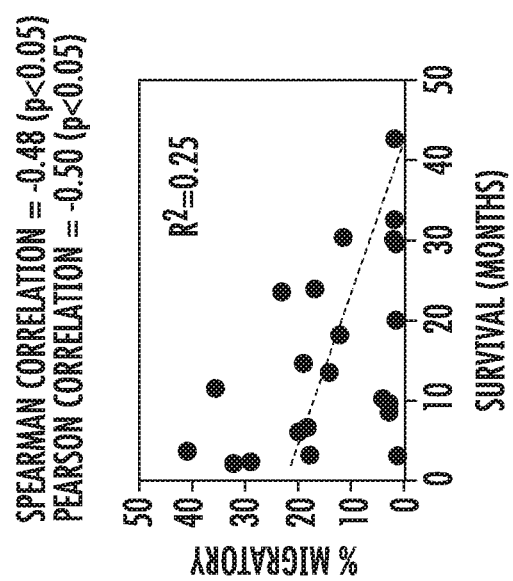

Metastatic propensity assay is amenable to a wide range of imaging techniques: Numerous imaging techniques were used to image an embodiment of the invention in which a PDMS fluidic layer is bonded to a glass coverslip layer. Cells were imaged using lens-free holography (FIG. 10A), which has an approximately 5 mm×5 mm field of view. Cells were clearly visible in the channels upon digitally zooming in (inset, FIG. 10A). Additionally, cells in the device were imaged using phase contrast microscopy (FIG. 10B) and a combination of phase contrast and fluorescence microscopy (FIG. 10C; a subset of cells was tagged with a fluorescent marker and appears green in the image).

Example 9

Brain tumors of glioblastoma multiforme from human patients receiving treatment at Johns Hopkins Hospital were resected and samples of cells from the tumors were collected using protocols similar to those described for breast cancer tumors. Sample aliquots of cells from each patient were then placed in the microfluidic apparatus to identify their migratory behavior and assess their invasiveness.

As shown in FIG. 1, cells were identified as migratory (i.e., cells that entered the migratory channel and entered one of the two outlet ends during the observational interval) and the percentage of cells in the sample that were migratory was calculated. The percentage of migratory cells in the patient sample was then correlated with patient survival time in months. A cutoff of 14.5% migratory cells was established by computing the mean % migratory value and separating the patients above or below this mean value. The data was then plotted as a Kaplan-Meier graph. The graph shows a difference in survival with p=0.016. The patients' survival times were compared to the 14.6 month standard average, to arrive at a group with high survival (>14.6 mo.) and a low survival group (<14.6 mo.). The data was then correlated to the percentage of cells in their sample that were identified as migratory. The inventors found a three-fold difference in median survival times of patients with <14.5% migratory cells in their sample vs. >14.5% migratory cells.

The inventors then further analyzed the data based on which outlet ends the migratory cells entered and/or exited in those samples. FIG. 2. shows the same type of analysis as FIG. 1, but the correlation was to those migratory cells entering the wide (20 μm) outlet end. As one can see, after normalizing the data, there was significant correlation of median survival, with >11.4% wide entering cells correlated with lower survival times than with <11.4% entering the wide outlet end with a p=0.014.

The inventors then analyzed the migratory cells entering the narrow (3 μm) outlet end (FIG. 3). Here, is a normalized graph of the data with a cutoff of 1.8%, the inventors did not observe a significant correlation of migratory cells entering the narrow outlet end with low survivability in these patients. The median survival time was about two-fold greater for those patients with <1.8% migratory cells entering the narrow outlet end. However, when looking at the normalized patient data, the inventors found a clearly significant correlation between survival time and the percentage of cells entered the wide outlet end (FIG. 4). With an 85.7% cutoff, the mean survival time for patients with less wide outlet end entry cells was almost two-fold greater, and patients with >85.7% narrow outlet end entry had significantly lower than average survival times of 8.9 vs. 18.8 months.

The inventors then analyzed the normalized narrow outlet end entry data in the same manner as FIG. 4. The inventors divided the groups into two cohorts of >14.28% wide outlet end entry, and <14.28% wide outlet end entry. The Kaplan-Meier survival graph shows a significant difference between each of the curves. When plotted, the data show that patients with the greatest proportion of narrow outlet end entry cells had the longest median survival times (23.3 months), greater than three-fold over the group with the lowest proportion of narrow outlet end entry cells (8.5 months).

Example 10

The cutoff and the amount of time during which cell migration is observed (experiment duration) can be optimized to allow the invention to identify metastatic and nonmetastatic cell populations from different types of cancer. For the breast epithelial cell lines and breast cancer cell lines described in FIG. 8, the accuracy, sensitivity and specificity of the invention are displayed in FIG. 17 across a wide range of cutoff values and experiment durations. The maximum value for accuracy was 96%, and was observed under three pairs of conditions: 7% cutoff and 13 hours, 8% and 12 hours, and 8% and 13 hours. Under each of these pairs of conditions, the sensitivity is 90% and the specificity is 100%.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for identifying the invasiveness of at least one cancer cell in a sample, the method comprising:
   a) obtaining the at least one cancer cell from the sample;
   b) incubating the at least one cancer cell for a period time sufficient to allow the at least one cancer cell to seed at the base of a migratory channel of an integrative microfluidic apparatus;
   c) imaging, by an imaging system, the at least one cancer cell in the integrative microfluidic apparatus for a period of time sufficient to allow migration of migratory cancer cells of the at least one cancer cell through the migratory channel; and d) determining a respective cancer cell of the at least one cancer cell is invasive when the respective cancer cell migrates through the migratory channel of the integrative microfluidic apparatus, wherein the migratory channel comprises:
- a body segment having sufficiently reduced dimensions so as to allow only one migratory cancer cell of the at least one cancer cell to enter into a first end of the migratory channel at a time, and
- a first branch and a second branch extending from a second end of the body segment, wherein the first branch and the second branch each have respective widths, and wherein the width of the first branch is different than the width of the second branch, wherein the second end of the body segment and the first and second branches meet at the bifurcation point of the migratory channel, and wherein the respective migratory cancer cell migrates through the migratory channel by entering the first end of the migratory channel and passing through the bifurcation point of the migratory channel to enter the first branch or the second branch.

2. The method of claim 1, wherein the sample is from a subject.

3. The method of claim 2, wherein the subject has glioblastoma multiforme.

4. The method of claim 1, further comprising isolating the at least one migratory cancer cell identified as being invasive.

5. The method of claim 1, wherein in step d), the at least one migratory cancer cell is invasive when the at least one cancer cell migrates through the migratory channel of the integrative microfluidic apparatus comprising the body segment and into one or more of the outlet ends of the integrative microfluidic apparatus.

6. The method of claim 1, wherein in step d), the at least one migratory cancer cell is invasive when the at least one cancer cell migrates through the migratory channel of the integrative microfluidic apparatus comprising the body segment and exited out of the one or more of the outlet ends of the integrative microfluidic apparatus.

7. The method of claim 1, wherein the at least one migratory cancer cell are imaged for 6 to 12 hours.

8. The method of claim 1, wherein the at least one cancer cell is imaged using a method selected from the group consisting of phase contrast, brightfield, differential interference contrast, fluorescence, and confocal microscopy and in-line holography.

9. The method of claim 1, wherein the first and the second branches of the migratory channel are connected to the body segment of the migratory channel at a bifurcation of the migration channel.

* * * * *